United States Patent [19]
Stern et al.

[11] Patent Number: 6,123,938
[45] Date of Patent: Sep. 26, 2000

[54] HUMAN URINARY HYALURONIDASE

[75] Inventors: Robert Stern; Anthony Csóka; Gregory I. Frost; Tim M. Wong, all of San Francisco, Calif.

[73] Assignee: The Regents of the University of California, Oakland, Calif.

[21] Appl. No.: 08/987,743

[22] Filed: Dec. 9, 1997

Related U.S. Application Data

[63] Continuation-in-part of application No. 08/733,360, Oct. 17, 1996.

[51] Int. Cl.[7] .......................... A61K 38/46; A61K 38/00; C07K 1/00
[52] U.S. Cl. ...................... 424/94.62; 530/350; 530/828; 530/834; 514/2; 514/12; 514/21
[58] Field of Search ..................................... 530/350, 828, 530/834; 514/2, 12, 21; 424/94.62

[56] References Cited

FOREIGN PATENT DOCUMENTS 57-132881  8/1982  Japan .

OTHER PUBLICATIONS

Reiger et al (Glossary of Genetics and Cytogenetics, Classical and Molecular, 4th Ed., Springer–Verlag, Berlin, p. 17), 1976.

Frost, et al., "Purification, Cloning, and Expression of Human Plasma Hyaluronidase," *Biochemical and Biophysical Research Communications* 236:10–15 (1997).

*Primary Examiner*—Susan Ungar
*Attorney, Agent, or Firm*—Carol L. Francis; Bozicevic, Field & Francis LLP

[57] ABSTRACT

The present invention is based on the purification and sequencing of isozymes of plasma hyaluronidase (pHAse) found in urine. Specifically, urine contains two hyaluronidases (HAses): 1) a 57 kDa HAse that is apparently the same as the 57 kDa HAse found in plasma; and 2) a 45 kDa HAse, which is found in urine but not plasma. The smaller urine isozyme is composed of two disulfide-linked polypeptides produced by endoproteolytic cleavage of the 57 kDa isoform. The present invention thus features a urinary hyaluronidase (uHAse) polypeptide and nucleotide sequences encoding a Chain A polypeptide and a Chain B polypeptide, the two polypeptides of which uHAse is composed. In a particular aspect, the uHAse is a human uHAse (huHAse), preferably a huHAse composed of the Chain A and B polypeptides having SEQ ID NOS: 2 and 4, respectively. In related aspects the invention features polynucleotide sequence encoding Chain A and Chain B polypeptides, preferably having the sequences of SEQ ID NOS: 1 and 3, respectively. In addition, the invention features polynucleotide sequences that hybridize under stringent conditions to SEQ ID NOS: 1 and 3. In related aspects the invention features expression vectors and host cells comprising polynucleotides that encode uHAse polypeptide Chains A and B. The present invention also features antibodies that bind specifically to uHAse, and methods for producing uHAse.

9 Claims, 4 Drawing Sheets

FIG. 2

HUMAN URINARY HYALURONIDASE

This application is a continuation-in-part of U.S. application Ser. No. 08/733,360, filed Oct. 17, 1996, which application is hereby incorporated by reference.

STATEMENT REGARDING FEDERALLY SPONSORED RESEARCH

This invention was made with government support under grant nos. CA44768, CA58207, and GM46765, awarded by the National Institutes of Health. The government may have certain rights in this invention.

FIELD OF THE INVENTION

This invention relates generally to the field of β-1,4-endoglycosidases, particularly hyaluronidases.

BACKGROUND OF THE INVENTION

Hyaluronidases (HAses; E.C. 3.1.25) are a group of neutral- and acid-active enzymes found throughout the animal kingdom in diverse organisms. Hyaluronidases degrade hyaluronan (HA; also known as hyaluronic acid) and, to a lesser extent, chondroitin sulfates (for a review, see Kreil et al. 1995 *Protein Sci.* 4:1666–9). Vertebrate hyaluronidases are separated into two general classes: 1) the neutral hyaluronidases, such as the predominantly sperm-associated protein PH20 (Liu et al. 1996 *Proc. Natl. Acad. Sci. USA* 93:7832–7; Primakoff et al. 1985 *J. Cell Biol.* 101:2239–44; Lin et al. 1993 *Proc. Natl. Acad. Sci. USA* 90:10071–5); and 2) the acid-active hyaluronidases, which have a distinct pH optimum between pH 3.5 to 4.0 and have been described in extracts of liver (Fiszer-Szafarz et al. 1995 *Acta Biochim Pol.* 42:31–3), kidney (Komender et al. 1973 *Bull. Acad. Pol. Sci.* (*Biol. J.* 21:637–41), lung (Thet et al. 1983 *Biochem. Biophys. Res. Commun.* 117:71–7), brain (Margolis et al. 1972 *J. Neutrochem.* 19:2325–32), skin (Cashman et al. 1969 *Arch. Biochem. Biophys.* 135:387–95), placenta, macrophages, fibroblasts (Lien et al. 1990 *Biochim Biophys. Acta* 1034:318–25; Ruggiero et al. 1987 *J. Dent. Res.* 66:1283–7), and human plasma (De Salegui et al. 1967 *Arch. Biochem. Biophys.* 120:60–67).

Human urine exhibits a high specific hyaluronidase activity (approximately 100-fold that of human plasma HAse activity) (Fiszer-Szafarz et al. supra; Dicker et al. 1966 *J Physiol* (*Lond*) 186:110–120; Cobbin et al. 1962 *J Physiol* (*Lond*) 163:168–174). Urine hyaluronidase may play a role in the action of antidiuretic hormones by increasing the permeability of the nephron walls, which have an ECM rich in HA (Cobbin et al. supra; Ginetzinsky et al. 1958 *Nature* 182:1218–1219). However, examination of this hypothesis and further characterization of the HAse activity of urine has proved elusive, mainly because the activity is present at such low concentrations.

Hyaluronan, the main substrate for hyaluronidase, is a repeating disaccharide of $[G1cNAc\beta1-4G1cUA\beta1-3]_n$ that exists in vivo as a high molecular weight linear polysaccharide. Degradation of hyaluronan by hyaluronidase is accomplished by either cleavage of β-N-acetyl-hexosamine-[1→4]-glycosidic bonds or cleavage at β-gluconorate-[1→3]-N-acetylglucosamine bonds. Hyaluronan is found in mammals predominantly in connective tissues, skin, cartilage, and in synovial fluid, and is also the main constituent of the vitreous of the eye. In connective tissue, the water of hydration associated with hyaluronan creates spaces between tissues, thus creating an environment conducive to cell movement and proliferation. Hyaluronan plays a key role in biological phenomena associated with cell motility including rapid development, regeneration, repair, embryogenesis, embryological development, wound healing, angiogenesis, and tumorigenesis (Toole 1991 *Cell Biol. Extracell. Matrix*, Hay (ed), Plenum Press, New York, 1384–1386; Bertrand et al. 1992 *Int. J. Cancer* 52:1–6; Knudson et al, 1993 *FASEB J.* 7:1233–1241). In addition, hyaluronan levels correlate with tumor aggressiveness (Ozello et al. 1960 *Cancer Res.* 20:600–604; Takeuchi et al. 1976, *Cancer Res.* 36:2133–2139; Kimata et al. 1983 *Cancer Res.* 43:1347–1354).

Hyaluronidase is useful as a therapeutic in the treatment of diseases associated with excess hyaluronan and to enhance circulation of physiological fluids and/or therapeutic agents at the site of administration. For example, hyaluronidase has been used to reduce intraocular pressure in the eyes of glaucoma patients through degradation of hyaluronan within the vitreous humor (U.S. Pat. No. 4,820,516, issued Apr. 11, 1989). Hyaluronidase has also been used in cancer therapy as a "spreading agent" to enhance the activity of chemotherapeutics and/or the accessibility of tumors to chemotherapeutics (Schüller et al., 1991, *Proc. Amer. Assoc. Cancer Res.* 32:173, abstract no. 1034; Czejka et al., 1990, *Pharmazie* 45:H.9) and has been used in combination with other chemotherapeutic agents in the treatment of a variety of cancers including urinary bladder cancer (Horn et al., 1985, *J. Surg. Oncol.*, 28:304–307), squamous cell carcinoma (Kohno et al., 94, *J. Cancer Res. Oncol.*, 120:293–297), breast cancer (Beckenlehner et al., 1992, *J. Cancer Res. Oncol.* 118:591–596), and gastrointestinal cancer (Scheithauer et al., 1988, *Anticancer Res.* 8:391–396). Administration of hyaluronidase also induces responsiveness of previously chemotherapy-resistant tumors of the pancreas, stomach, colon, ovaries, and breast (Baumgartner et al., 1988, *Reg. Cancer Treat.* 1:55–58; Zänker et al., 1986, *Proc. Amer. Assoc. Cancer Res.* 27:390). When added extracelluarly, hyaluronidase prevents growth of tumors transplanted into mice (De Maeyer et al., 1992, *Int. J. Cancer* 51:657–660), inhibits tumor formation upon exposure to carcinogens (Pawlowski et al., 1979, *Int. J. Cancer* 23:105–109; Haberman et al., 1981, *Proceedings of the 17th Annual Meeting of the American Society of Clinical Oncology*, Washington, D.C., 22:105, abstract no. 415, and is effective in the treatment of brain cancer (gliomas) when following intravenous or intramuscular injection (PCT published application no. WO88/02261, Apr. 7, 1988).

Hyaluronidase expression, and levels of hyaluron, have been associated with tumor development and progression. Levels of a secreted neutral hyaluronidase activity in carcinomas derived from ovary (Miura et al. 1995 *Anal. Biochem.* 225:333–40), prostate (Lokeshwar et al. 1996 *Cancer Res* 56:651–7), brain, melanocyte, and colon (Liu et al. 1996 *Proc. Natl. Acad. Sci. USA* 93:7832–7837) are higher than in normal tissue. This secreted neutral hyaluronidase activity appears similar or identical to the neutral hyaluronidase activity of the sperm hyaluronidase PH20. In contrast to neutral activity, the acid active HAse activity is significantly decreased in metastatic carcinomas of the lung, breast, and colon (Northrup et al. 1973 *Clin. Biochem.* 6:220–8; Kolarova et al. 1970 *Neoplasma* 17:641–8). Further, mice having an allele of the hyal-1 locus that is associated with lower levels of serum hyaluronidase activity exhibit faster rates of growth of transplanted tumors than mice having an hyal-1 allele that is associated with 3-fold higher hyaluronidase activity levels (Fiszer-Szafarz et al. 1989 *Somat. Cell. Mol. Genet.* 15:79–83; De Maeyer et al. supra).

At present, the only hyaluronidase activity available for clinical use is a hyaluronidase isolated from a testicular extract from cattle (WYDASE®, Wyeth-Ayerst). The bovine extract is not optimum not only because of its non-human source, but also because the extract contains multiple types of hyaluronidases and other as yet undefined components. Recently we purified and cloned the major hyaluronidase activity of human plasma, which we termed HYAL1 (also known as hpHAse), and observed that the protein is homologous to PH-20, with 40% amino acid identity (Frost et al. 1997 *Biochem Biophys Res Commun* 236:10–15). Highest levels of expression of the HYAL1 mRNA were found in liver and kidney. The production of monoclonal antibodies was essential for purification of sufficient enzyme for microsequencing.

There is a clear need in the field for additional purified acid-active hyaluronidases that can be used in therapy and other applications. The present invention addresses this problem.

SUMMARY OF THE INVENTION

The present invention is based on the purification and sequencing of isozymes of plasma hyaluronidase (pHAse) found in urine. Specifically, urine contains two hyaluronidases (HAses): 1) a 57 kDa HAse that is apparently the same as the 57 kDa HAse found in plasma; and 2) a 45 kDa HAse, which is found in urine but not plasma. The smaller urine isozyme is composed of two disulfide-linked polypeptides produced by endoproteolytic cleavage of the 57kDa isoform. The present invention thus features a urinary hyaluronidase (uHAse) polypeptide and nucleotide sequences encoding a Chain A polypeptide and a Chain B polypeptide, the two polypeptides of which uHAse is composed. In a particular aspect, the uHAse is a human uHAse (huHAse), preferably a huHAse composed of the Chain A and B polypeptides having SEQ ID NOS: 2 and 4, respectively. In related aspects the invention features polynucleotide sequence encoding Chain A and Chain B polypeptides, preferably having the sequences of SEQ ID NOS: 1 and 3, respectively. In addition, the invention features polynucleotide sequences that hybridize under stringent conditions to SEQ ID NOS: 1 and 3. In related aspects the invention features expression vectors and host cells comprising polynucleotides that encode uHAse polypeptide Chains A and B. The present invention also features antibodies that bind specifically to uHAse, and methods for producing uHAse.

Yet another aspect of the invention relates to use of uHAse isozymes and specific antibodies thereto for the diagnosis and treatment of human disease.

A primary object of the invention is to provide a purified hyaluronidase, huHAse, which can be used in a variety of clinical therapies including cancer therapy, particularly cancers associated with a defect in the tumor suppressor gene LuCa-1

Another object of the invention is to provide purified uHAse and polynucleotides encoding the polypeptides of uHAse for use in expression of uHAse (e.g, in a recombinant host cell).

An advantage of the present invention is that purified huHAse is more appropriate for therapeutic uses than the presently available commercial formulations of hyaluronidase which are from a non-human source, which contain two hyaluronidases (rather than one), and which, as determined by SDS-PAGE analysis, are very crude mixtures containing various proteins, including several unidentified proteins and proteins having various biological activities including anticoagulant activities (Doctor et al., Thrombosis Res. 30:565–571). Purified huHAse provides a "clean" source of hyaluronidase, is less likely to induce some of the side effects associated with the presently available commercial formulation, and allows better control of the level of activity associated with specific dosages.

These and other objects, advantages and features of the present invention will become apparent to those persons skilled in the art upon reading the details of the invention as more fully set forth below.

BRIEF DESCRIPTION OF THE DRAWINGS

FIG. 2 is a schematic showing the amino acid sequences of human plasma hyaluronidase (hpHAse, also known as HYAL1; SEQ ID NO: 6), murine hyaluronidase (Hyal1; SEQ ID NO: 7), and the sites of endoproteolytic cleavage that lead to production of the Chain A and Chain B polypeptides (SEQ ID NOS: 2 and 4) of urine HAse. The sequence of the intervening amino acid sequence deleted during huHAse production (SEQ ID NO: 9), as well as the hpHAse signal sequence (SEQ ID NO: 8), are also shown.

DETAILED DESCRIPTION OF THE PREFERRED EMBODIMENTS

Figure 1:
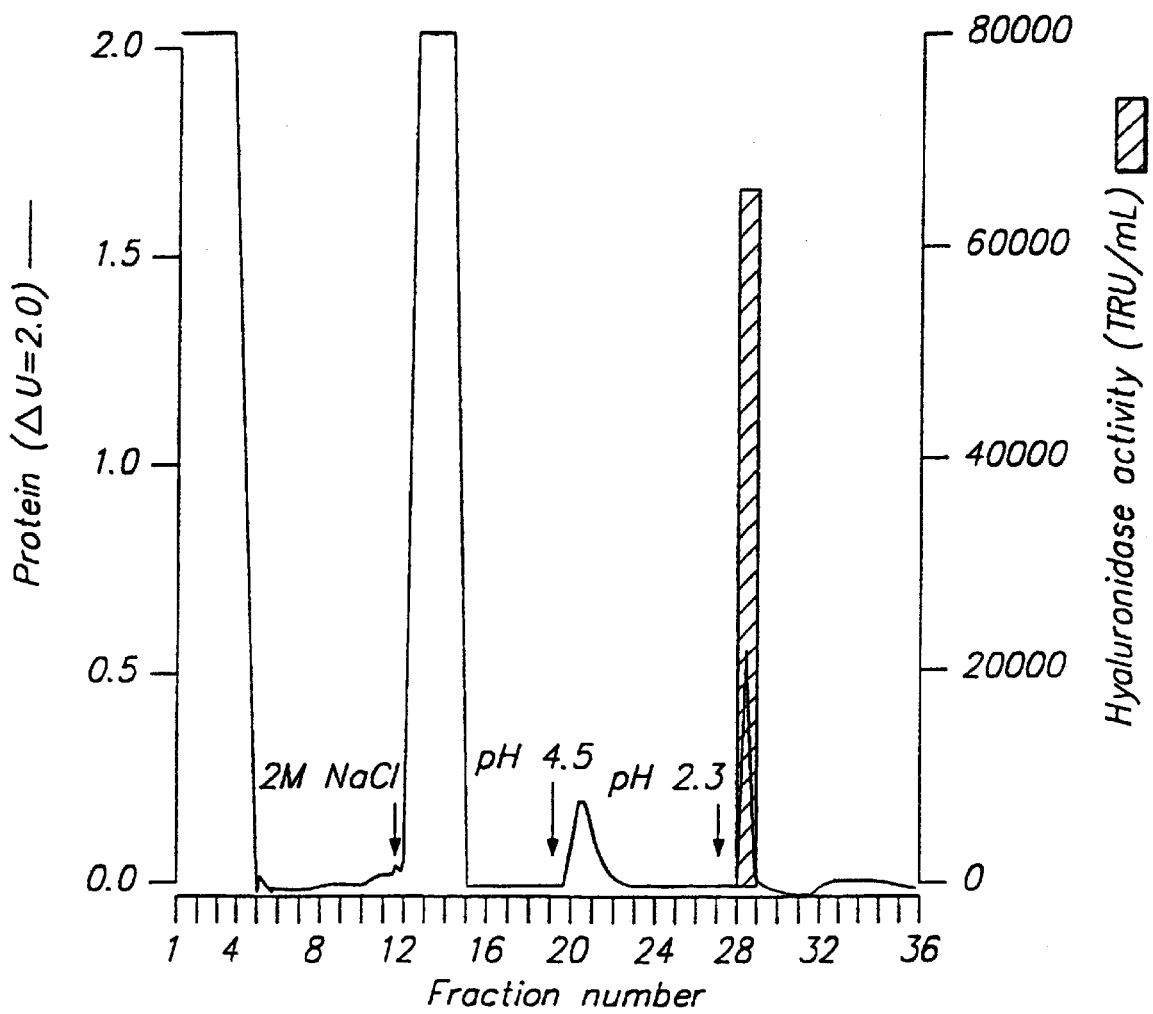
FIG. 1 is a graph showing monoclonal antibody affinity chromatography of urinary hyaluronidase. Protein is represented by the solid line, scale on the left (Abs. 280, DU=2.0). Hyaluronidase activity is represented by the shaded bar, scale on the right. Fractions 1–4 contain the final 6 ml of urine passing through the column. Beginning at fraction 12 the column was washed with 2M NaCl, and at fraction 19 with Na acetate pH 4.5. All of the hyaluronidase eluted during the Na citrate pH 2.3 wash in fraction 28.

Before the present purified hyaluronidase and DNA encoding same are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a transformed cell containing DNA encoding a hyaluronidase" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

Definitions

By "acid active hyaluronidase" or "aaHAse" is meant a hyaluronidase having β-1,4-endoglycosidase activity in the cleavage of hyaluronan and a pH optimum of HAse activity at about pH 3.7. aaHAse as used herein encompasses human plasma hyaluronidase and human urinary hyaluronidase.

By "human plasma hyaluronidase" and "hpHAse" is meant a hyaluronidase naturally found in human plasma and human urine and having the following characteristics: 1) β-1,4-endoglycosidase activity in the cleavage of hyaluron; 2) a pH optimum of HAse activity at about pH 3.7; 3) a molecular weight of about 57 kDa as determined by 12.5% SDS-PAGE non-reducing gel electrophoresis; 4) a specific enzymatic activity of about $2 \times 10^5$ to $8 \times 10^5$ turbidity reducing units (TRU)/mg protein following purification; 5) an isoelectric point, as determined by elution in chromatofocusing on Mono-P f.p.l.c., of pH 6.5; 6) partitioning into the Triton X-114 detergent-rich phase upon temperature-induced detergent phase extraction; 7) a fatty acid post-translational modification (e.g., a lipid anchor) that is resistant to cleavage by phospholipase C, phospholipase D, and N-glycosidase-F; 8) at least two N-linked glycosylation sites; and 9) has the amino acid sequence:

MAAHLLPICALFLTLLDMAQGFRGPLLPNRPF
TTVWNANTQWCLERHGVDVDVSVFDVVANP
GQTFRGPDMTIFYSSSQLGTYPYYTPTGEPVF
GGLPQNASLIAHLARTFQDILAAIPAPDFSGLA
VIDWEAWRPRWAFNWDTKDIYRQRSRA
LVQAQHPDWPAPQVEAVAQDQFQGAARAW
MAGTLQLGRALRRGLWGFYGFPDCYNYDF
LSPNYTGQCPSGIRAQNDQLGWLWGQSRALY
PSIYMPAVLEGTGKSQMYVQHRVAEAFRVAVA
AGDPNLPVLPYVQIFYDTTNHFLPLDELEHSL
GESAAQGAAGVVLWVSWENTRTKESCQAIK
EYMDTTLGPFILNVTSGALLCSQALCSGHGR
CVRRTSHPKALLLLNPASPSIQLTPGGGPLS
LRGALSLEDQAQMAVEFKCRCYPGWQAPWCE
RKSMW (SEQ ID NO: 6)

where MAAHLLPICALFLTLLDMAQG (SEQ ID NO: 8) is a signal sequence cleaved during post-translational modification."

By "urine hyaluronidase" or "uHAse" is meant a hyaluronidase naturally found in urine (but not present in significant or detectable amounts in plasma) and having the following characteristics: 1) β-1,4-endoglycosidase activity in the cleavage of hyaluron; 2) a pH optimum of HAse activity at about pH 3.8; 3) a molecular weight of about 45 kDa as determined by gel zymography using 12.5% SDS-PAGE non-reducing gel electrophoresis; and 9) two disulfide-linked polypeptide chains (Chain A and Chain B). Where the uHAse is human uHAse (huHAse), Chain A polypeptide has the amino acid sequence of SEQ ID NO: 2 and Chain B polypeptide has the amino acid sequence of SEQ ID NO: 4. "uHAse" as used herein is meant to encompass uHAse having the amino acid sequence of naturally-occurring uHAse, as well as all naturally-occurring allelic variants and modified uHAse which contains amino acid substitution(s), deletion(s), and/or addition (s) and the like relative to the naturally-occurring amino acid sequence. Preferably, "uHAse" encompasses uHAse polypeptides that are biologically active (e.g., can bind anti-uHAse antibodies and/or exhibit hyaluronidase activity). Human uHAse is exemplary of a uHAse of the invention.

By "Chain A polypeptide" is mean a polypeptide chain of uHAse which is of higher molecular weight relative to Chain B polypeptide of uHAse. "Chain A polypeptide" as used herein is meant to encompass uHAse Chain A polypeptides having the amino acid sequence of naturally-occurring uHAse Chain A polypeptide, as well as all naturally-occurring allelic variants and modified uHAse Chain A polypeptide which contains amino acid substitution(s), deletion(s), and/or addition(s) and the like relative to the naturally-occurring amino acid sequence. Preferably, "Chain A polypeptide" encompasses Chain A polypeptides that are biologically active (e.g., can bind anti-uHAse antibodies). Human Chain A polypeptide having the amino acid sequence of SEQ ID NO: 2 is an exemplary uHAse Chain A polypeptide of the invention.

By "Chain B polypeptide" is mean a polypeptide chain of uHAse which is of lower molecular weight relative to Chain A polypeptide of uHAse. "Chain B polypeptide" as used herein is meant to encompass uHAse Chain B polypeptides having the amino acid sequence of naturally-occurring uHAse Chain B polypeptide, as well as all naturally-occurring allelic variants and modified uHAse Chain B polypeptide which contains amino acid substitution(s), deletion(s), and/or addition(s) and the like relative to the naturally-occurring amino acid sequence. Preferably, "Chain B polypeptide" encompasses Chain B polypeptides that are biologically active (e.g., can bind anti-uHAse antibodies). Human Chain B polypeptide having the amino acid sequence of SEQ ID NO: 4 is an exemplary uHAse Chain B polypeptide of the invention.

By "native uHAse" is meant uHAse that is folded in its naturally-occurring configuration (i.e., uHAse is not denatured and is composed of linked Chain A and Chain B polypeptides). Where the native uHAse does not comprise the entire amino acid sequence of naturally-occurring uHAse, native uHAse polypeptides are those polypeptides that, when folded, mimic a three-dimensional epitope of native, full-length uHAse such that antibodies that bind native uHAse bind to the uHAse polypeptide. "Native uHAse" encompasses both uHAse naturally found in urine, as well as uHAse that is recombinantly produced (e.g., by expression in a mammalian cell).

By "polypeptide" is meant any chain of amino acids, regardless of length or post-translational modification (e.g., glycosylation. phosphorylation. or fatty acid chain modification).

By a "substantially pure polypeptide" is meant, for example, uHAse, Chain A polypeptide, or Chain B polypeptide that has been separated from components which naturally accompany it (e.g., a substantially pure uHAse polypeptide purified from human urine is substantially free of components normally associated with human urine). Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, uHAse polypeptide. A substantially pure uHAse polypeptide can be obtained, for example, by extraction from a natural source (e.g., mammalian plasma, preferably human plasma); by expression of a recombinant nucleic acid encoding uHAse polypeptide; or by chemically synthesizing the protein. Purity can be measured by any appropriate method, e.g., chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "antibody" is meant an immunoglobulin protein that is capable of binding an antigen. Antibody as used herein is meant to include the entire antibody as well as any antibody fragments (e.g. $F(ab')_2$, Fab', Fab, Fv) capable of binding the epitope, antigen or antigenic fragment of interest. Antibodies of the invention are immunoreactive or immunospecific for and therefore specifically and selectively bind to native uHAse polypeptide. Anti-uHAse antibodies are preferably immunospecific (i.e., not substantially cross-reactive with related materials). Antibodies may be polyclonal or monoclonal, preferably monoclonal.

By "purified antibody" is meant one that is sufficiently free of other proteins, carbohydrates, and lipids with which it is naturally associated. Such an antibody "preferentially binds" to an antigenic uHAse polypeptide, i.e., does not substantially recognize and bind to other antigenically-unrelated molecules.

By "binds specifically" is meant high avidity and/or high affinity binding of an antibody to a specific polypeptide i.e., epitope of uHAse. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to huHAse than to other components in human plasma. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to native uHAse with a binding affinity of $10^7$ liters/mole or more, preferably $10^8$ l/mole or more, even more preferably $10^9$ l/mole or more, are said to bind specifically to uHAse. In general, an antibody with a binding affinity of $10^4$ l/mole or less is not useful in that it will not bind an antigen at a detectable level using conventional methodology currently used.

By "anti-native uHAse antibody" or "anti-uHAse antibody" is meant an antibody that specifically binds native (i.e., non-denatured) uHAse. Preferably, such antibodies can be used to immunopurify (e.g., by immunoprecipitation or immunoaffinity column chromatography) naturally-occurring uHAse from human plasma and/or recombinant huHAse expressed by, for example, mammalian cells.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule.

"uHAse polynucleotide" is meant to refer to any polynucleotide sequence encoding all or a portion of a uHAse and thus encompasses sequences encoding Chain A polypeptide, Chain B polypeptide, and both Chain A and Chain B polypeptides. Where the uHAse polynucleotide encodes both Chain A and Chain B polypeptides, the uHAse-encoding sequence may be substantially free of plasma HAse-encoding sequences that do not encode at least a portion of a uHAse (e.g., the uHAse-encoding sequence does not include nucleotide sequences encoding the portion of plasma HAse that is eliminated during endoproteolytic processing of plasma HAse to produce uHAse Chain A and Chain B polypeptides).

By "antisense polynucleotide" is meant polynucleotide having a nucleotide sequence complementary to a given polynucleotide sequence including polynucleotide sequences associated with the transcription or translation of the given polynucleotide sequence, where the antisense polynucleotide is capable of hybridizing to a uHAse polynucleotide sequence. Of particular interest are antisense polynucleotides capable of inhibiting transcription and/or translation of a uHAse polynucleotide either in vitro or in vivo.

By "substantially identical" is meant a polypeptide or nucleic acid exhibiting at last 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease (e.g., cancer) from occurring in a subject who may be predisposed to the disease but has not yet been diagnosed as having it; (b) inhibiting the disease, i.e., arresting its development; or (c) relieving the disease, i.e., causing regression of the disease. The invention is directed toward treatment of patients having or susceptible to cancer associated with a defect in HAse activity, e.g., cancer associated with a defect in the LuCa-1 gene, the gene that encodes hpHAse and huHAse.

By "therapeutically effective amount of a substantially pure uHAse polypeptide" is meant an amount of a substantially pure uHAse polypeptide effective to facilitate a desired therapeutic effect. The precise desired therapeutic effect will vary according to the condition to be treated. For example, the desired degradation of hyaluronan is the desired therapeutic effect where uHAse is administered to the subject in the treatment of a condition associated with excess hyaluron, undesirable cell motility (e.g., tumor cell metastasis), and/or to enhance circulation of physiological fluids at the site of administration and/or inhibit tumor growth or progression. Where uHAse is administered to treat a patient having or susceptible to cancer associated with a LuCa-1 defect, one desired therapeutic effects include, but are not necessarily limited to, an inhibition of tumor cell growth and a decrease in the tumor cell's threshold to apoptosis (i.e., increase the cell's sensitivity to triggers to programmed cell death).

By "LuCa-1 defect" is meant a genetic defect in a cell at chromosome position 3p. 21.3 associated with a decreased level of hpHAse activity relative to hpHAse activity levels in normal cells and/or associated with a decreased level of hpHAse activity in the serum or plasma of the affected patient (e.g., due to decreased expression of hpHAse or expression of a defective hpHAse). For example, plasma from patients have a LuCa-1 defect-associated lung cancer exhibits about 50% less hpHAse activity than plasma from normal patients (i.e., patients who do not have a LuCa-1 defect-associated cancer). Normal human plasma exhibits about 15 rTRU/mg hpHAse activity as determined using the HAse assay of Frost et al. (1997 Anal. Biochem. 251:263–9; see also U.S. patent application Ser. No. 08/733,360, filed Oct. 17, 1996. The hpHAse activity of plasma from LuCa-1 defect-associated lung cancer patients is about 7.5 rTRU/mg.

By "having or susceptible to a condition associated with a LuCa-1 defect" is meant to describe a patient having a heterozygous or homozygous defect at the LuCa-1 locus that is associated with decreased levels of hpHAse (e.g., serum hpHAse or urine hpHAse, preferably serum hpHAse) relative to hpHAse levels associated with normal patients (i.e., patients having no LuCa-1 defect that results in altered hpHAse levels).

The invention will now be described in further detail.

Purification of Hyaluronidase Isozymes from Urine

Purification of uHAse from urine can be accomplished by either biochemical methods or through use of an anti-uHAse antibody (e.g., immunoprecipitation or immunoaffinity). Each of these methods is described in detail below.

Biochemical uHAse Purification Method

Acid active hyaluronidase activity such as that associated with uHAse can be significantly enriched and/or purified using temperature-induced detergent phase extraction with a non-ionic detergent (e.g., Triton X-114). In general, a sample comprising or suspected of comprising uHAse is dissolved in a solution comprising a non-ionic detergent at low temperature (e.g., substantially below room temperature, preferably less than about 15° C., more preferably about 4° C.). The sample can be, for example, urine, preferably mammalian urine, more preferably human urine, or can be a sample containing a recombinant uHAse polypeptide.

After the sample is dissolved, the temperature of the solution is raised to at least room temperature or above (preferably above about 25° C., more preferably about 37° C.), thereby resulting in formation of detergent-rich and detergent-poor phases. The uHAse partitions into the detergent-rich phase. The detergent-rich phase can be further enriched for uHAse by removal of the detergent-rich phase and repetition of temperature-induced detergent phase extraction. Repeating this temperature-induced detergent phase extraction three times results in at least about 10-fold, preferably at least about 20-fold, more preferably at least about 60-fold enrichment of uHAse activity relative to uHAse activity in the starting material. The uHAse activity of the detergent-rich phase can be further enriched and purified by, for example, cation exchange chromatography and/or hydroxylapatite resin.

Generation and Identification of Anti-Native aaHAse Antibodies

Antibodies that specifically bind uHAse can be generated according to the methods described in U.S. Application Ser. No. 08/733,360, filed Oct. 17, 1996, which application is incorporated herein by reference. Briefly, antibodies that bind uHAse can be generated by using uHAse, or another aaHAse that is antigenically similar to uHAse (e.g., another aaHAse such as hpHAse), as an antigen in the immunization of a mammal (e.g., mouse, rat, rabbit, goat); hybridoma cell lines are then produced according to methods well known and routine in the art (see, for example, Harlow and Lane, 1988, Antibodies: A Laboratory Manual, Cold Spring Harbor Laboratory Press, Cold Spring Harbor, N.Y.; Schrier et al., 1980, Hybridoma Techniques, Cold Spring Harbor Laboratory Press, Cold Spring Harbor, N.Y.). The aaHAse used in the antigenic preparation can be purified from the source in which it naturally occurs (e.g., huHAse purified from human urine), recombinant aaHAse, biologically active (e.g., antigenic and/or enzymatically active) aaHAse polypeptides, native aaHAse, and/or denatured aaHAse polypeptides. Where the aaHAse is a recombinant aaHAse, the recombinant aaHAse can comprise the amino acid sequence of a naturally-occurring aaHAse, or can be modified relative to native aaHAse (e.g., by amino acid substitution, deletion, or addition (e.g., fusion protein)). Preferably, the antigenic preparation is native aaHAse (e.g., aaHAse purified from the source in which it naturally occurs or recombinant, full-length aaHAse).

The antibodies secreted by the hybridoma cell lines are screened in the anti-native aaHAse antibody assay described in U.S. Application Ser. No. 08/733,360, filed Oct. 17, 1996, which application is incorporated herein by reference. In general, the assay involves an insoluble support (e.g., the surface of a well of a microtiter plate) to which is bound: 1) an anti-antibody; and 2) detectably labeled hyaluronic acid (HA). The anti-antibody is capable of binding antibodies produced by the aaHAse-immunized mammalian host regardless of antigen specificity. For example, where the immunized host is a mouse, the anti-antibody is a goat anti-mouse antibody (i.e., an antibody from a goat immunized with mouse antibodies). Preferably, the anti-antibody binds an Fc portion of antibodies produced by the aaHAse-immunized mammalian host, and may specifically bind immunoglobulin classes or subclasses (e.g., specifically bind IgG or an IgG subclass such as $IgG_1$ or $IgG_2$). Preferably, the anti-antibody is covalently bound to the surface of the insoluble support. The detectably labeled HA is preferably biotinylated HA (bHA) in the above-described HAse assay, and is preferably covalently bound to the surface of the insoluble plate as described above.

The anti-aaHAse antibody assay takes advantage of the fact that aaHAses do not bind their HA substrates under non-acidic conditions (i.e., under conditions in which the aaHAse is not enzymatically active). In general, the assay is performed by contacting the candidate antibody with a sample comprising native aaHAse to allow for formation of native aaHAse/antibody complexes. Preferably, this contacting step is performed at a non-acidic, preferably neutral, pH. The sample is then contacted under non-acidic (preferably neutral) conditions with the insoluble support having bound anti-antibody and detectably labeled HA to allow for formation of native aaHAse/antibody/anti-antibody complexes by binding of the anti-antibody to the candidate antibody. Preferably, excess or unbound material is washed away with a non-acidic (preferably neutral) solution.

The wash buffer is replaced with an acidic solution having a pH that allows for enzymatic activity of the aaHAse. Preferably the acidic solution has a pH that approximates the optimum pH for HAse activity of the aaHAse. For example, where the aaHAse is uHAse, the acidic solution preferably has a pH of about 3.8; where the aaHAse is hpHAse, the acidic solution preferably has a pH of about 3.7. The sample is incubated with the insoluble support for a time sufficient for degradation of the detectably labeled HA by the immunoprecipitated aaHAse bound in the native aaHAse/antibody/anti-antibody complex, preferably about 60 min. The samples are then washed to remove degraded HA and undegraded HA is detected by virtue of its label. For example, where the detectable label is biotin, undegraded bHA is detected as described in the above-described HAse assay. Degradation of HA is correlated with the presence of aaHAse in the sample which in turn is correlated with the presence of an anti-native aaHAse antibody. The general characteristics of antibodies of the invention are described below.

Anti-uHAse Antibody Characteristic: Antibody/antigen Binding Forces

The forces that hold an antigen and antibody together can be classified into four general areas: (1) electrostatic; (2) hydrogen bonding; (3) hydrophobic; and (4) Van der Waals. Electrostatic forces are due to the attraction between oppositely charged ionic groups on two protein side-chains. The force of attraction (F) is inversely proportional to the square of the distance (d) between the charges. Hydrogen bonding forces are due to formation of reversible hydrogen bridges between hydrophilic groups such as —OH, —NH$_2$ and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalanine tend to associate in an aqueous environment. Lastly, Van der Waals are forces created between molecules by interaction between the external electron clouds. Further information about the different types of forces is known in the art (see, e.g., *Essential Immunology*, I. M. Roitt, ed., 6th Ed. Blackwell Scientific Publications, 1988.

Useful antibodies of the present invention exhibit all of these forces. By obtaining an accumulation of these forces in greater amounts, it is possible to obtain an antibody that has a high degree of affinity or binding strength to native uHAse, and in particular an antibody that has a high degree of binding strength to uHAse in the material in which it naturally occurs (e.g., human urine).

Anti-uHAse Antibody Affinity

The binding affinity between an antibody and an antigen is an accumulative measurement of all of the forces described above. Standard procedures for carrying out such measurements are known in the art and can be directly applied to measure the affinity of anti-native uHAse antibodies of the invention.

One standard method for measuring antibody/antigen binding affinity uses a dialysis sac, composed of a material permeable to the antigen but impermeable to the antibody. Antigens that bind completely or partially to antibodies are placed within the dialysis sac in a solvent (e.g., water). The sac is then placed within a larger container which does not contain antibodies or antigen but contains only the solvent. Since only the antigen can diffuse through the dialysis membrane the concentration of the antigen within the dialysis sac and the concentration of the antigen within the outer larger container will attempt to reach an equilibrium. The amount of antigen that remains bound to antibody in the dialysis sac and the amount that disassociated from the antibody are calculated by determining the antigen concentrations within the dialysis sac and within the solvent outside the dialysis sac. By constantly renewing the solvent (e.g., the water) within the surrounding container so as to remove any diffused antigen, it is possible to totally disassociate the antibody from antigen within the dialysis sac. If the surrounding solvent is not renewed, the system will reach an equilibrium, and the equilibrium constant (K) of the reaction, i.e., the association and disassociation between the antibody and antigen, can be calculated. The equilibrium constant (K) is calculated as an amount equal to the concentration of antibody bound to antigen within the dialysis sac divided by the concentration of free antibody combining sites times the concentration of free antigen. The equilibrium constant or "K" value is generally measured in terms of liters per mole. The K value is a measure of the difference in free energy ($\Delta G$) between the antigen and antibody in the free state as compared with the complexed form of the antigen and antibody. Anti-native uHAse antibodies having an affinity or K value of $10^7$ l/mole to $10^9$ l/mole or more are preferred.

Antibody Avidity

As indicated above the term "affinity" describes the binding of an antibody to a single antigen determinate. The term "avidity" is used to express the interaction of an antibody with a multivalent antigen. The factors that contribute to avidity are complex and include both the heterogeneity of the antibodies in a given serum that are directed against each determinate on the antigen and the heterogeneity of the determinants themselves. The multivalence of most antigens leads to an interesting "bonus" effect in which the binding of two antigen molecules by an antibody is always greater, usually many fold greater, than the arithmetic sum of the individual antibody links. Thus, it can be understood that the measured avidity between an antiserum and a multivalent antigen will be somewhat greater than the affinity between an antibody and a single antigen determinate.

Other Uses of Anti-uHAse Antibodies

Anti-uHAse antibodies are useful in various imnmunotechniques, including immunopurification and immunodetection techniques. Anti-uHAse antibodies useful in such immunotechniques may be either polyclonal or monoclonal antibodies, preferably monoclonal antibodies.

Preferably, anti-uHAse antibodies useful in immunotechniques exhibit an equilibrium or affinity constant ($K_d$) of at least $10^7$ l/mole to $10^9$ l/mole or greater. The binding affinity of $10^7$ l/mole or more may be due to (1) a single monoclonal antibody (i.e., large numbers of one kind of antibody) (2) a plurality of different monoclonal antibodies (e.g., large numbers of each of five different monoclonal antibodies) or (3) large numbers of polyclonal antibodies. It is also possible to use combinations or (1)–(3).

Preferred antibodies bind 50% or more of native uHAse in a sample. However, this may be accomplished by using several different antibodies as per (1)–(3) above. An increased number of different antibodies is generally more effective than a single antibody in binding a larger percentage of antigen in a sample. Thus, a synergistic effect can be obtained by combining combinations of two or more antibodies which bind native uHAse, i.e., by combining two or more antibodies that have a binding affinity $K_a$ for native uHAse of $10^7$ l/mole or more.

Immunopurification Using Anti-native aaBHAse Antibodies

Antibodies that specifically bind uHAse can be used in, for example, immunopurification of uHAse from its naturally occurring source (e.g., HAse isozymes from human urine) or from a source of recombinant uHAse polypeptide production. Immunopurification techniques useful in the purification of uHAse include, but are not limited to, immunoprecipitation, immunoaffinity isolation on beads, immunoaffinity column chromatography, and other methods well known in the art. Anti-native uHAse antibodies useful in immunopurification of uHAse include any anti-native aaHAse antibody that specifically binds native uHAse (e.g., anti-huHAse and anti-hpHAse antibodies). The immunopurification methods using the antibodies of the invention can use a single anti-native uHAse antibody (e.g, a monoclonal or polyclonal antibody, preferably a monoclonal antibody) or multiple anti-native uHAse antibodies.

In addition, the anti-native uHAse antibodies of the invention can be used to prepare a device for immunopurification of native uHAse, preferably native uHAse or a polypeptide thereof, more preferably native huHAse. In general, such devices are prepared by covalently binding an anti-native uHAse antibody to an insoluble support (e.g., bead, affinity column component (e.g., resin), or other insoluble support used in immunoaffinity purification). Alternatively, the antibody may be bound to a metal particle which allows separation of anti-native uHAse-uHAse complexes from a solution by use of a magnetized column. The anti-uHAse antibody may be a monoclonal or polyclonal antibody, preferably a monoclonal antibody. The antibodies bound to the insoluble support (or otherwise employed in purification) may also comprise a mixture of anti-native uHAse antibodies to provide a device that can bind to at least 50% of the native uHAse in the sample. Such immunopurification devices can be used to isolate aaHAse from a source in which it naturally occurs (e.g., huHAse from raw urine) or from a source of recombinantly-produced uHAse.

Qualitative and Quantitative Immunodetection Using Anti-native uHAse Antibodies

Anti-native uHAse antibodies can be used in immunodetection assay to detect and, where desirable, quantitate uHAse in a sample. Immunodetection assays using anti-native uHAse antibodies can be designed in a variety of ways. For example, anti-native uHAse antibodies can be used to produce an assay device comprising anti-native uHAse antibodies bound to a soluble support (e.g., an immunoassay column, beads, or wells of a microtiter plate). Methods for covalent or non-covalent attachment of an antibody to a soluble support are well known in the art. A sample suspected of containing an uHAse is then contacted with the assay device to allow formation of anti-native uHAse antibody-uHAse complexes. The anti-native uHAse-uHAse complexes can then be detected by virtue of a uHAse activity associated with the complex as described in the anti-native uHAse assay described above, or by contacting the complex with a second detectably-labeled anti-native uHAse antibody.

By "detectably labeled antibody", "detectably labeled anti-uHAse antibody" or "detectably labeled anti-uHAse antibody fragment" is meant an antibody (or antibody fragment that retains antigen binding specificity), having an attached detectable label. The detectable label is normally attached by chemical conjugation; where the label is a polypeptide, the label can be attached by genetic engineering techniques. Detectable labels may be selected from a variety of such labels known in the art, but normally are radioisotopes, fluorophores, paramagnetic labels, enzymes (e.g., horseradish peroxidase), or other moieties or compounds that either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

Alternatively, detectably labeled anti-native uHAse antibodies can be directly used to detect and/or quantify uHAse in a sample. For example, detectably labeled anti-native huHAse antibodies can be contacted with a tissue sample suspected of having a LuCa-1/hpHAse defect (e.g., a tissue sample derived from breast, ovaries, or lung) for a time sufficient to allow for formation of complexes between the anti-native huHAse antibody and huHAse in the sample. Binding of the anti-native huHAse antibody can then be detected and/or quantified by virtue of a detectable label bound to the anti-native huHAse antibody. Alternatively, binding of the anti-native huHAse antibody can be detected using an antibody that binds the anti-native huHAse antibody. Binding of anti-native huHAse antibody to a tissue sample can then be compared to anti-native huHAse antibody binding to a control sample (e.g., a normal sample having no LuCa-1/hpHAse defect and/or a sample containing tissue associated with a LuCa-1/hpHAse defect) and the antibody binding correlated with the presence or absence of a LuCa-1/hpHAse defect in the patient. Alternatively or in addition anti-uHAse antibodies can be used to detect huHAse in samples of patient receiving huHAse therapy, to correlate HAse levels in a sample with tumor progression in the patient, responsiveness to therapy, and/or uptake of huHAse by the patient's body. Where uHAse is detected in urine, the levels of uHAse can be correlated with susceptibility to and/or the presence of a LuCa-1 defect associated disease state and/or the severity of such disease, as well as with the levels of uHAse present following administration of uHAse during therapy.

uHAse-Encoding Polynucleotides

The polynucleotide sequences encoding uHAse (e.g., the polynucleotide sequence encoding Chain A and Chain B of uHAse) may be cDNA or genomic DNA or a fragment thereof. The gene may be introduced into an appropriate vector for extrachromosomal maintenance or for integration into the host. The term "cDNA" as used herein is intended to include all nucleic acids that share the arrangement of sequence elements found in native mature mRNA species, where sequence elements are exons and 3' and 5' non-coding regions.

In contrast, genomic uHAse sequences may have non-contiguous open reading frames, where introns interrupt the protein coding regions. Genomic sequences can also comprise the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The nucleic acid compositions of the subject invention may encode all or a part of the Chain A and/or Chain B huHAse polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than about 50 nt to 100 nt are useful for production of the encoded polypeptide. For PCR amplification, it is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The uHAse-encoding sequences are isolated and obtained in substantial purity, generally as other than an intact mammalian chromosome. Usually, the DNA will be obtained substantially free of other nucleic acid sequences that do not include a uHAse-encoding sequence (e.g., a Chain A- or Chain B-encoding sequence) or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying homologs of uHAse (e.g., homologs of huHAse). Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. 1990 J Mol Biol 215:403–10.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under high stringency conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. Primate species, particularly human; rodents, such as rats and mice, canines, felines, bovine, opines, equine, yeast, *Drosophila, Caenhorabditis,* etc.

uHAse-encoding DNA can also be used to identify expression of the gene in a biological specimen. The manner in which one probes cells for the presence of particular nucleotide sequences, as genomic DNA or RNA, is well established in the literature and does not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to a uHAse sequence is indicative of uHAse expression in the sample.

uHAse-encoding sequences (e.g., Chain A- or Chain B-encoding sequences) may be modified for a number of purposes, particularly where they will be used intracellularly, for example, by being joined to a nucleic acid cleaving agent, e.g. a chelated metal ion, such as iron or chromium for cleavage of the gene; or the like. Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

Methods of Making uHAse

In addition to the purification procedure outlined above, uHAse polypeptides (e.g,. huHAse polypeptides) can be made by standard synthetic techniques, or by using recombinant DNA technology and expressed in bacterial, yeast, or mammalian cells using standard techniques. As used herein, the term "uHAse" includes natural, recombinant, and modified forms of the protein unless the context in which the term is used clearly indicates otherwise.

Chemical Synthesis uHAse polypeptides can be synthesized based on the amino acid sequences described herein and variations thereof by standard solid-phase methods using the tert-butyloxy-carbonyl and benzyl protection strategy described in Clark-Lewis et al., *P.N.A.S., USA*, 90:3574–3577 (1993) and Clark-Lewis et al., *Biochemistry*, 30:3128–3135 (1991). After deprotection with hydrogen fluoride, the proteins are folded by air oxidation and purified by reverse-phase HPLC. Purity is determined by reverse-phase HPLC and isoelectric focusing. Amino acid incorporation is monitored during synthesis, and the final composition is determined by amino acid analysis. The correct covalent structure of the protein can be confirmed using ion-spray mass spectrometry (SCIEX APIII).

Recombinant DNA Techniques for Synthesis of uHAse Polypeptides

As discussed in the examples below, LuCa-1 and hpHAse are identical, and huHAse is an endoproteolytic cleavage product of hpHAse. The amino acid sequences of hpHAse and LuCa-1 vary at four amino acid residue positions (where the Met at the N-terminus of the signal sequence is counted as the first amino acid residue): 1) an Ala is substituted for Gly at the $3^{rd}$ residue within the signal sequence ; 2) a Val is substituted for Leu at the 27th amino acid residue; 3) an Arg is substituted for Gly at the 191$^{st}$ amino acid residue; and 4) a Glu is substituted for Leu at the 300$^{th}$ amino acid residue. However, the two proteins are otherwise identical in amino acid sequence and immunological and biochemical characteristics.

The nucleotide sequence encoding hpHAse is identical to the sequence encoding LuCa-1, except for the variations in the codons encoding the amino acids as described above. Thus, the nucleotide sequence encoding LuCa-1 is the nucleotide sequence encoding hpHAse. Moreover, since uHAse is a proteolytically processed from hpHAse polypeptide, the nucleotide sequence encoding hpHAse contains the sequences that encode the Chain A and Chain B polypeptides of huHAse. The LuCa-1/hpHAse gene has been isolated and sequenced (Bader et al. GenBank accession no. U03056, NID G532973, submitted Nov. 1, 1993). The amino acid and nucleotide sequences of LuCa-1 as described by Bader et al. are provided as SEQ ID NOS: 15 and 16, respectively.

The nucleotide sequence encoding a HAse can be isolated according to any one of a variety of methods well known to those of ordinary skill in the art. For example, DNA encoding HAse can be isolated from either a cDNA library or from a genomic DNA library by either hybridization or expression cloning methods. Alternatively, the DNA can be isolated using standard polymerase chain reaction (PCR) amplification of synthetic oligonucleotide primers, e.g., as described in Mullis et al., U.S. Pat. No. 4,800,159, or expression cloning methods well known in the art (see, e.g., Sambrook et al. 1989 *Molecular Cloning: A Laboratory Manual*, 2nd Ed., Cold Spring Harbor Laboratory Press, Cold Spring Harbor, N.Y.). Where hybridization or PCR is used to identify DNA encoding HAse, the sequence of the oligonucleotide probes or primers can be based upon the amino acid or nucleotide sequence of LuCa-1 provided above.

The sequence of isolated HAse polypeptide-encoding DNA can be determined using methods well known in the art (see, for example, Sambrook et al., supra . Following sequence confirmation, the resulting clones can be used to, for example, identify homologs of HAse (e.g., other human alleles encoding HAse or an acid active serum hyaluronidase of another mammalian species (e.g., dog, rat, mouse, primate, cow), and/or to transform a target host cell for expression of DNA encoding a polypeptide of uHAse (e.g., Chain A or Chain B polypeptide).

Expression of HAse Polypeptides

Expression of a uHAse polypeptide (e.g., a uHAse Chain A polypeptide, or a uHAse Chain B polypeptide), is accomplished by inserting a nucleotide sequence encoding a uHAse polypeptide into a nucleic acid vector such that a promoter in the construct is operably linked to, for example, the Chain A- or Chain B-encoding sequence. The construct can then be used to transform a mammalian, insect, yeast, or bacterial host cell. Numerous, commercially available vectors useful in recombinant polypeptide expression can be used. Preferably the vector is capable of replication in both eukaryotic and prokaryotic hosts, and are generally composed of a bacterial origin of replication and a eukaryotic promoter operably linked to a DNA of interest. A number of vectors suitable for stable transfection of mammalian, insect, yeast, and bacterial cells are available to the public from a wide variety of sources, e.g., the American Type Culture Collection, Rockville, Md. Suitable host cells, as well as methods for constructing stably-transformed host cell lines, are also publicly available, e.g., Pouwels et al., 1985, *Cloning Vectors: A Laboratory Manual*, Ausubel et al., 1989, *Current Protocols in Molecular Biology*, John Wiley & Sons, New York; and Sambrook et al., supra. Mammalian and yeast cells are preferred host cells.

Techniques for preparation of constructs containing of nucleic acid sequence of interest and for obtaining expression of exogenous DNA or RNA sequences in a host cell are well known in the art (see, for example, Kormal et al., 1987, *Proc. Natl. Acad. Sci. USA*, 84:2150–2154; Sambrook et al., supra; each of which are hereby incorporated by reference with respect to methods and compositions for eukaryotic expression of a DNA of interest). Expression of recombinant uHAse polypeptides (e.g., Chain A or Chain B polypeptide) can be assayed by immunological procedures, such as Western blot or immunoprecipitation analysis of recombinant cell extracts, or by the HAse activity assay as described by Frost et al. (1997 *Anal. Biochem.* 251:263–9; see also U.S. patent application Ser. No. 08/733,360, filed Oct. 17, 1996).

For example, uHAse polypeptides according to the invention can be produced by transformation of a suitable host cell (e.g., bacterial, yeast, or mammalian cell, preferably mammalian cell) with a uHAse polypeptide-encoding nucleotide sequence(s) (e.g., a nucleotide sequence encoding Chain A and a nucleotide sequence encoding Chain B) in a suitable expression vehicle, and culturing the transformed cells under conditions that promote expression of the encoded polypeptide. Where the host cell is a mammalian cell, the vector is preferably designed to allow for secretion of uHAse into the culture medium. The method of transformation and the choice of expression vehicle will depend on the host system selected. Those skilled in the field of molecular biology will understand that any of a wide variety of prokaryotic and eukaryotic expression systems may be used to produce uHAse polypeptides of the invention. The precise host cell used is not critical to the invention.

Identification of Biologically Active uHAse and uHAse Polypeptides uHAse, Chain A, or Chain B polypeptide-encoding DNAs can encode all or a portion of uHAse, Chain A, or Chain B. Preferably, the expressed polypeptide is biologically active, e.g., exhibits acid active hyaluronidase activity in the cleavage of hyaluronan and/or can be bound by an anti-native uHAse antibody. In general, once information regarding the ability of a protein to elicit antibodies and/or information regarding an enzymatic or other biological activity of a protein of interest is known, methods for identification of biologically active polypeptides of the full-length protein are routine to the ordinarily skilled artisan, particularly where the nucleotide sequence and/or amino acid sequence encoding the protein of interest (here huHAse, Chain A polypeptide, or Chain B polypeptide) is provided as in the present case.

Biologically active uHAse polypeptides can be identified by using the HAse activity described by Frost et al. (1997 *Anal. Biochem.* 251:263–9; see also U.S. patent application Ser. No. 08/733,360, filed Oct. 17, 1996), or by using conventional HAse activity assays (e.g., the ELISA-like hyaluronan assay (Stern et al., 1992, *Matrix* 12:391–403) or substrate gel zymography (Guentenhoener et al., 1992, *Matrix* 12:388–396)). Alternatively, biologically active uHAse polypeptides can be detected by binding of an anti-native uHAse antibody to a component of the transformed host cell supernatant and/or lysate. uHAse polypeptides preferably exhibit at least 25%, more preferably 50%, still more preferably 75%, even more preferably 95% of the activity of native uHAse.

Identification of Hyaluronidases Homologous to uHAse

DNA encoding hyaluronidases homologous to uHAse (e.g., contain conservative amino acid substitutions relative to a native uHAse) can be accomplished by screening various cDNA or genomic DNA libraries by hybridization or PCR using oligonucleotides based upon the DNA sequence and/or amino acid sequence of a uHAse, Chain A polypeptide, and/or Chain B polypeptide. Alternatively the oligonucleotides used may be degenerate, e.g., based upon a selected amino acid sequence of uHAse or designed so as to allow detection or amplification of DNA encoding a uHAse-like amino acid sequence having conservative amino acid substitutions and/or to take into account the frequency of codon usage in the mammalian species DNA to be screened. Such "degenerate oligonucleotide probes" can be used in combination in order to increase the sensitivity of the hybridization screen, and to identify and isolate uHAse analogs and orthologs in other species or variant alleles encoding uHAse in humans. Methods for designing and using degenerate oligonucleotide probes to identify a protein for which an amino acid and/or nucleotide sequence, as well as methods for hybridization and PCR techniques for screening and isolation of homologous DNAs, are routine and well known in the art (see, for example, Sambrook et al. supra).

Therapies Using uHAse Polypeptides

The substantially pure native uHAse polypeptides (e.g., uHAse polypeptides that are not associated with the components of plasma from which uHAse is purified) of the invention can be used in a variety of applications including human and veterinary therapies, either alone or in combination with other therapeutic agents. Purified uHAse of the invention can generally be used in place of neutral HASE formulations or WYDASE™, where the condition to be treated is associated with excess hyaluronic acid and/or therapy is designed to increase HAse activity generally (i.e., the conventional neutral hyaluronidase-containing formulation is not used to treat a specific defect in neutral HAse activity, but rather provides a HAse (neutral or acid active) activity). Use of an acid active HASE is preferred to use of neutral HAses since acid active HAses can yield a controlled degradation of HA substrate and does not degrade all components of the extracellular matrix in the patient.

Administration of uHAse may be advantageous over administration of other HAses due to uHAse's lower molecular weight, which can allow the enzyme to enter cells more readily than the other, higher molecular weight HAses. Thus uHAse will have better bioavailability than HAses of higher molecular weight.

uHAse can be used in the treatment of diseases associated with excess hyaluron, to enhance circulation of physiological fluids at the site of administration (e.g., as a spreading agent, e.g., by subcutaneous or topical application (e.g., in cosmetic formulations such as cosmetic creams), and/or as an anti-cancer agent either alone or in combination with chemotherapeutic agents. For example, huHAse can be administered to a patient to facilitate clysis, particularly hypodermoclysis.

Of particular interest is the administration of huHAse to patients suffering from stroke or a myocardial infarction (e.g., by infusion) (see, e.g., Maclean et al. 1976 Science 194:199–200; Opie 1980 Am Heart J. 100:531–52). Administration of Hase to patients suffering from myocardial infarction can facilitate a decrease in pressure upon myocardial tissues, prevent tissue necrosis, and relieve edema. Use of uHAse in treatment of myocardial infarct patients is advantageous over use of other HAses since uHAse lacks the three EGF repeats present at the carboxy terminus of other HAses (e.g., hpHAse), indicating that the activity of uHAse will not be inhibited by heparin. Heparin is often administered during heart attacks and is a very powerful inhibitor of HAse activity of other HAses containing this EGF motif. Because uHAse lacks the EGF motif, and thus will not be inhibited by heparin, the clinician need not be concerned that co-administration of heparin with uHAse will render uHAse inactive.

Methods for administration, and amounts of huHAse administered, for treatment of myocardial infarction can be based upon methods of administration of bovine testicular hyaluronidase and amounts administered (see, e.g., Wolf et al. 1982 J. Pharmacol. Exper. Therap. 222:331–7; Braunwald et al. 1976 Am. J. Cardiol. 37:550–6; DeGiovanni et al. 1961 Br. Heart J. 45:350; DeOliveira et al. 1959 Am. Heart J. 57:712–22; Kloner et al. 1978 Circulation 58:220–6; Kloner et al. 1977 Am. J. Cardiol. 40:43–9; Koven et al. 1975 J. Trauma 15:992–8; Maclean et al. 1978 J. Clin. Invest. 61:541–51; Maclean et al. 1976 Science 194:199–200; Maroko et al. 1975 Ann. Intern. Med. 82:516–20; Maroko et al. 1977 N. Engl. J. Med. 296:896–903; Maroko et al. 1972 Circulation 46:430–7; Salete 1980 Clin. Biochem. 13:92–94; Snell et al. 1971 J. Clin. Invest. 50:2614–25; Wolf et al. 1981 Circ. Res. 48:88–95).

Furthermore, uHAse can also have therapeutic effects when administered to patients having certain lysosomal storage diseases associated with a defect in hyaluronidase (see, e.g., Natowicz et al. 1996 N. Engl. J. Med. 335:1029–33). huHAse can used therapeutically by direct administration of hyaluronidase (e.g., intracellularly or intravenously) as a form of shunt pathway. Lysosomal storage disease amenable to uHAse therapy are those diseases that result in accumulation of $[GlcNAc\beta1-4GlcUA\beta1-3]_n$ (GAGs) due to a defective mannose-6-phosphate pathway. uHAse can degrade these accumulated GAGs under a nonfunctional cellular system since HASE activity does not depend upon the mannose-6-phosphate pathway (Herd et al. 1976 Proc. Soc. Experim. Biol. Med. 151:642–9).

uHAse can also be used in the treatment of edema associated with brain tumors, particularly that associated with glioblastoma multiform. The edema associated with brain tumors results from the accumulation of hyaluronan in the non-cancerous portions of the brain adjacent the tumor. Administration of hyaluronidase to the sites of hyaluronan accumulation (e.g., by intravenous injection or via a shunt) can relieve the edema associated with such malignancies by degrading the excess hyaluronan at these sites. Thus, hyaluronidase is successful in the treatment of brain tumors not only in the reduction of the tumor mass and inhibition of tumor growth and/or metastasis, but it also is useful in relieving edema associated with the malignancy. uHAse can be administered for treatment of edema in a manner similar to that for administration of bovine testicular hyaluronidase to treat edema (see, e.g., SaEarp Arq. Braz. Med. 44:217–20).

Of particular interest is the use of uHAse biologically active polypeptides in the treatment of cancer. uHAse can be used as a chemotherapeutic agent (alone or in combination with other chemotherapeutics) in the treatment of any of a variety of cancers, particularly invasive tumors. For example, uHAse can be used in the treatment of small lung cell carcinoma, squamous lung cell carcinoma, as well as cancers of the breast, ovaries or any other cancer associated with depressed levels of HAse activity or with a defective LuCa-1 (hpHAse) gene (e.g., a LuCa-1 gene that does not provide for expression of adequate hpHAse levels or encodes a defective hpHAse that does not provide for an adequate level of hyaluronidase activity).

uHAse can also be used to increase the sensitivity of tumors that are resistant to conventional chemotherapy. In one embodiment, huHAse is administered to a patient having a tumor associated with a LuCa-1 defect in an amount effective to increase diffusion around the tumor site (e.g., to increase circulation of chemotherapeutic factors (e.g., to facilitate circulation and/or concentrations of chemotherapeutic agents in and around the tumor site), inhibit tumor cell motility (e.g., by HA degradation) and/or to lower the tumor cell(s) threshold of apoptosis (i.e., bring the tumor cell(s) to a state of anoikis), a state that renders the tumor cell(s) more susceptible to the action of chemotherapeutic agents or other agents that may facilitate cell death, preferably preferentially facilitate programmed cell death of cells in anoikis. Chemotherapeutic agents as used herein is meant to encompass all molecules, synthetic (e.g, cisplatin) as well as naturally-occurring (e.g., tumor necrosis factor (TNF)), that facilitate inhibition of tumor cell growth, and preferably facilitate, more preferably preferentially facilitate tumor cell death.

Patients having or susceptible to a disease or condition that is amenable to treatment with uHAse can be identified using a variety of conventional methods, or by using an assay device of the invention having bound anti-native uHAse antibodies as described above to determine HASE levels in, for example, urine, blood, plasma, or serum, and correlate such levels with a LuCa-1 defect. For example, where the patient is suspected of having or of being susceptible to a condition associated with decreased HAse activity, a biological sample (e.g., blood, serum, or plasma) can be obtained from the patient and assayed using the HAse assay and/or inmmunoassays using anti-native HAse antibodies (e.g., anti-hpHAse or anti-huHAse antibodies) as described above.

The route of administration and amount of uHAse administered will vary widely according to the disease to be treated, and various patient variables including size, weight, age, disease severity, and responsiveness to therapy. Methods for determining the appropriate route of administration and dosage are generally determined on a case-by-case basis by the attending physician. Such determinations are routine to one of ordinary skill in the art (see, for example, *Harrison's Principles of Internal Medicine*, 11th Ed., 1987). For example, where huHAse is used to facilitate hypodermoclysis, a solution containing huHAse is administered by subcutaneous injection to facilitate absorption of the solution (e.g., nutrient, body fluid replacement, or blood pressure increasing solution). Preferably, uHAse is administered by injection, e.g., parenteral injection including subcutaneous, intramuscular, intraorbital, intracapsular, and intravenous injection. In one embodiment, native uHAse is administered in a liposome (see, e.g., *Liposome Technology*, G. Gregoriadis, ed., 1984, CRC Press, Boca Raton, Fla.).

In some therapeutic applications of uHAse, it may be desirable to modify uHAse to provide one or more desirable characteristics. For example, it may be desirable to increase its biological half-life by, for example, modification of the polypeptide. Various methods for increasing the half-life of a protein are well known in the art and include, for example, conjugation of the protein to polyethylene glycol moieties, i.e., PEGylation (see, for example, U.S. Pat. No. 4,179,337; U.S. Pat. No. 5,166,322; U.S. Pat. No. 5,206,344; Nucci et al., 1991, *Adv. Drug Delivery Rev.* 4:133–151; Zalipsky et al., 1991, "Polymeric Drugs and Drug Delivery Systems," ACS) conjugation of the protein to dextran (Maksimenko, 1986, *Bull. Exp. Biol. Med.* (*Russian*) 52:567–569), and deglycosylation of the protein by treatment with endoglycosidase F (Lace et al., 1990, *Carbohydrate Res.* 208:306–311).

The specific dosage appropriate for administration can be readily determined by one of ordinary skill in the art according to the factors discussed above (see, for example, *Harrison's Principles of Internal Medicine*, 11th Ed., 1987). In addition, the estimates for appropriate dosages in humans may be extrapolated from determinations of the level of enzymatic activity of Hase in vitro and/or dosages effective in animal studies. For example, 70–300 TRU hyaluronidase is effective in reducing the tumor load in a scid mouse. Given this information, the corresponding dosages in the average 70 kg human would range from about 250,000–1,200,000 TRU hyaluronidase. The amount of a uHAse polypeptide administered to a human patient is generally in the range of 1 TRU to 5,000,000 TRU of enzymatic activity, preferably between about 1,000 TRU to 2,500,000 TRU, more preferably between about 100,000 TRU to 1,500,000 TRU, normally between about 250,000 TRU and 1,200,000 TRU, with about 725,000 TRU representing average prescribed doses.

In one embodiment, a huHAse polypeptide is formulated in a 0.15 M saline solution containing huHAse at a concentration of about 150,000 TRU/cc. The formulation is then injected intravenously at 15,000 TRU/kg body weight of the patient. Alternatively, the enzyme formulation may also be injected subcutaneously to allow the hyaluronidase to perfuse around the tumor site.

Numerous other uses for human HAses, specifically urine HAse, more specifically human urine HAse, as well as uses for anti-HAse antibodies and HAse polypeptide-encoding nucleotide sequences are readily apparent to one of ordinary skill in the art.

DEPOSITS

The hybridoma cell lines 17E9 and 4D5, which produces an anti-hpHAse antibody that binds native hpHAse, has been deposited on behalf of The Regents of the University of California, 300 Lakeside Drive, 22nd Floor, Oakland, California 94612 with the American Type Culture Collection (ATCC), Rockville, Maryland, U.S.A. for patent purposes. The deposit of the hybridoma cell line 17E9 was received by the ATCC on Oct. 17, 1996, ATCC Designation HB-12213. The deposit of the hybridoma cell line 4D5 was received by the ATCC on Oct. 17, 1996, 1996, ATCC Designation HB-12214. The hybridoma cells were deposited under the conditions specified by the Budapest Treaty on the international recognition of the deposit of microorganisms (Budapest Treaty).

Availability of the deposited material is not to be construed as a license to practice the invention in contravention of the rights granted under the authority of any government in accordance with its patent laws.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Biochemical Purification of hpHAse Isozymes from Urine

The urinary isozymes of hpHAse were purified from human urine in a three-step biochemical procedure: 1) temperature-induced detergent phase extraction of human urine; 2) Fast Flow-S cation exchange chromatography; and 3) hydroxyl-apatite resin. Hyaluronidase activity and protein concentration were determined at each stage of purification, and the specific hyaluronidase activity calculated. Hyaluronidase activity was determined using the assay described in Frost et al. 1997 *Anal. Biochem.* 251:263–9 and U.S. patent application Ser. No. 08/733,360, filed Oct. 17, 1996. Protein concentration was determined by both absorbance at 280 nm and with the Biorad (Burlingame, Calif.) protein microassay kit (Tengblad 1979 *Biochim. Biophys. Acta* 578:281–289) in 96 well plates, using crystallized bovine serum albumin as a standard and read at 595 nM.

1) Temperature-induced detergent phase extraction

Two liters of human urine were routinely used for enzyme purifications. Two liters of chilled human urine were dissolved in a solution 0.02% Sodium Azide, 50 mM NaCl, 5% sucrose and 7.5% Triton X-114 (Boehringer Mannheim) were dissolved at 4° C. with stirring for 90 min followed by centrifugation at 10,000×g for 30 min to remove insoluble material. The urine was then subjected to temperature-induced phase extraction at 37° C. to separate the detergent-rich and detergent-poor phases. The extract was centrifuged at 10,000×g for 30 min at 37° C. to clarify the two phases. The detergent-rich phase was removed and diluted to 2 liters with cold 50 mM Hepes, pH 7.5, 0.15 M NaCl. The solution was then allowed to mix thoroughly on ice followed by repartitioning at 37° C. with centrifugation. This was repeated three times in order to increase the specific activity of the hyaluronidase that partitioned into the detergent phase.

2) Fast Flow-S cation exchange chromatography

The final detergent-rich phase from step 1) was diluted six-fold with 20 ml of equilibrated SP-Sepharose cation exchange resin (Pharmacia) in 25 mM Mes, pH 6.0 and stirred overnight at 4° C. The beads were collected through centrifugation and washed extensively with 25 mM Mes, pH 6.0, containing 46 mm octylglucoside (Boehringer Mannheim). Hyaluronidase was eluted from the beads through the addition of 0.3 M NaCl in Mes pH 6.0 buffer with several washes. The SP-Sepharose eluant was concentrated on a YM3 (Amicon) membrane and desalted into 10 mM $PO_4$ pH 7.4 with 25 mM NaCl, 46 mM octylglucoside on a f.p.l.c. Fast-Desalting column.

3) Hydroxyl-apatite resin

The hyaluronidase preparation from step 2) was combined with 10 ml of equilibrated hydroxylapatite resin (Biorad) and left on a rocker overnight at 4° C. huHAse did not adsorb to the resin under these conditions and was recovered in the supernatant. huHAse recovered in the supernatant was purified to homogeneity as determined by electrophoretic analysis on silver-stained 12.5% polyacrylamide gels on a Pharmacia Phast Gel System.

Results

The urinary hpHAse isozymes partitioned into the detergent-rich Triton X-114 phase, suggesting the urinary hpHAse isozymes contain a lipid modification similar to that of hpHAse. The isoelectric point of the urinary HASE activity was 6.5 as determined by elution in chromatofocusing on Mono-P f.p.l.c. Human urinary HASE activity immunoprecipitated with the anti-native hpHAse antibody 17E9 described in Frost et al. 1997 *Biochem. Biophys Res. Commun.* 236:10–15 and U.S. patent application Ser. No. 08/733,360, filed Oct. 17, 1996.

Gel zymography revealed two bands of HASE activity in crude plasma and urine samples. In plasma, HASE activity was detected in two bands corresponding to 57 kDa and 46–47 kDa; the 57 kDa band was the predominant species. In urine, HASE activity was also detected in two bands corresponding 57 kDa and 46–47 kDa; however, neither species was predominant (i.e., the bands appeared in the urine sample with equal intensity). These data suggested that hpHAse and the urinary hpHAse isozymes are present in plasma and urine, respectively, in two distinct modified forms (e.g., as a holoprotein and a proteolytic or otherwise modified fragment), or that there are two distinct acid active HASE proteins present in urine and in plasma.

Example 2

Immiunopurification of Human Urinary Hyaluronidase (huHAse)

hpHAse was purified, and anti-hpHAse antibodies produced, as described in Frost et al., 1997 *Biochem Biophys Res Commun.* 236:10–15 and U.S. patent application Ser. No. 08/733,360, filed Oct. 17, 1996. Two hybridoma cell lines 17E9 and 4D5, which secrete an anti-hpHAse antibody, were produced. The 17E9 antibody, which was successfully used in immunoprecipitation and immunopurification of hpHAse from human plasma and immunoprecipitation of the HASE activity associated with urine (see Example 1), was used in the immunopurification of huHAse from human urine. Three mg of purified 17E9 antibody was coupled to a 1 ml Hi-Trap-NHS-activated column (Pharmacia, Uppsala, Sweden) to produce an anti-HYAL1 affinity column as previously described (Frost et al. 1997 *Biochem Biophsy Res. Commun.* 236:10–15).

Twenty liters of human urine were collected from laboratory volunteers, concentrated to 1 liter and desalted into PBS on a CH2PRS cartridge concentrator fitted with a S3Y10 spiral cartridge (Amicon, Beverley, Mass., USA). To the concentrated urine, 1% Triton X-100, 1% sodium deoxycholate, 1% NP-40, and 0.02% sodium azide were added with stirring, followed by centrifugation at 10,000×g for 1 h to remove insoluble material. The urine was filtered through a 0.22 μm bottletop filter (Corning Costar Corp. Cambridge, Mass., USA) and applied to the anti-HYAL1 column on an F.P.L.C. system (Pharmacia) at 1 ml/min. The column was then washed with 5 ml of 2 M NaCl in 1% Triton X-100, followed by 0.1 M Na acetate pH 5.0, 0.1 M NaCl, 50 mM octylglucoside, and finally with 0.1 M Na citrate, pH 2.7, 0.1 M NaCl, 50 mM octylglucoside.

Fractions of 1.5 ml collected during the washing procedure were assayed for hyaluronidase activity using either a classic colorimetric assay (Reissig et al. 1955 *J. Biol. chem.* 217:959–66), the microtiter-based assay of Frost et al. (1997 *Anal. Biochem.* 9), or HA substrate gel zymography (Guntenhöner et al. 1992 *Matrix* 12:388–96). All of the assays were standardized to the Turbidity Reducing Unit (TRU) with commercial hyaluronidase (Sigma Type VI hyaluronidase) as a standard. One TRU of hyaluronidase is defined as the amount of enzyme that will decrease the turbidity-producing capacity of 0.2 mg HA to that of 0.1 mg HA in 30 min. at 37° C. (Tolksdorf et al. 1949 *J. Lab. Clin. Med.* 34:74–89). Protein concentrations were measured with the detergent-compatible Micro BCA assay (Pierce, Rockford, Ill., USA). Proteins were visualized with the Pharmacia Phast system on 12.5% SDS-PAGE gels according to the manufacturers instructions.

Levels of hyaluronidase activity in the pooled unconcentrated urine were approximately 4 TRU/ml with a protein concentration of 70 μg/ml. This equates to a total amount of activity of $8 \times 10^4$ TRU in 20,000 ml at a specific activity of 57 TRU/mg protein. This is approximately 100-fold greater than that of human plasma, which has a specific activity of 0.6 TRU/mg. All of the hyaluronidase present in urine was bound to the anti-hpHAse column. No activity was detected in the 2 M NaCl (fractions 12–15, FIG. 1) or the pH 4.5 wash (fractions 19–22, FIG. 1). All of the activity eluted as a very sharp peak during the subsequent pH 2.3 wash (fraction 28, FIG. 1). 62,000 TRU were recovered in this fraction, which represents a yield of 78%.

SDS-PAGE electrophoresis of column fraction 28 demonstrated that urine contains five proteins of 90, 57, 45, 28–30, and 14 kDa that bind to the monoclonal antibody. The 90 kDa protein disappeared at lower concentrations, or after reduction with 5% β-mercaptoethanol, and was probably a dimer of the 45 kDa activity. The size of the other proteins did not change after reduction. Only the 90, 57, and 45 kDa proteins possessed hyaluronidase activity on substrate gel zymography. The pattern of activity closely resembled that previously reported for rat liver lysosomal hyaluronidase, which consists of a doublet of activity on HA zymograms (Fiszer-Szafarz 1984 *Anal. Biochem.* 143:76–81). The smaller proteins of 28–30 and 14 kDa did not have hyaluronidase activity on substrate gel zymography. These proteins are not found in human plasma and their function is unknown.

Example 3

Sequence Analysis of huHAse

Fractions with hyaluronidase activity were concentrated by precipitation in 100% acetone at −20° C. overnight and resuspended in 40 μl Laemmli buffer (Laemmli 1970 *Nature* 227:680–5). The fractions were then separated in a 12% SDS-PAGE gel on a Mighty Small II' system (Hoefer Scientific Instruments, San Francisco, Calif., USA). After electrophoresis, the bands of protein were excised with a scalpel, extracted, and sequenced by Edman degradation.

The amino acid sequences obtained from the 57 kDa and 45 kDa isozymes are shown in Table 1. Sequence A from both isozymes is identical to that obtained from human plasma hyaluronidase (Frost et al. 1997 *Biochem Biophys Res. Commun.* 236:10–15). The sequences did not have significant homology to PH-20. This was not surprising since hpHAse and PH-20 are not homologous at their N-termini (Frost et al 1997 *Biochem Biophys Res. Commun.* 236:10–15). The lower molecular weight isozyme contained a second sequence (sequence B) that is derived from the last 25 amino acids of the C-terminus of hpHAse. This suggests that an internal cleavage had produced a smaller isozyme with two N-termini.

TABLE 1

N-terminal amino acid sequences of hpHAse and huHase

| Isozyme (Mol wt.) | N-terminal amino acid sequence |
| --- | --- |
| 57 kDa | Sequence A: FXGPLLPNRPFTTVWNXNTQW (SEQ ID NO: 10); |
| 45 kDa | Sequence A: FXGPLLPNXPFTTVWNA (SEQ ID NO: 11) |
|  | Sequence B: VEFKXRXYPGWQAPXXERK (SEQ ID NO: 12) |

Figure 2:
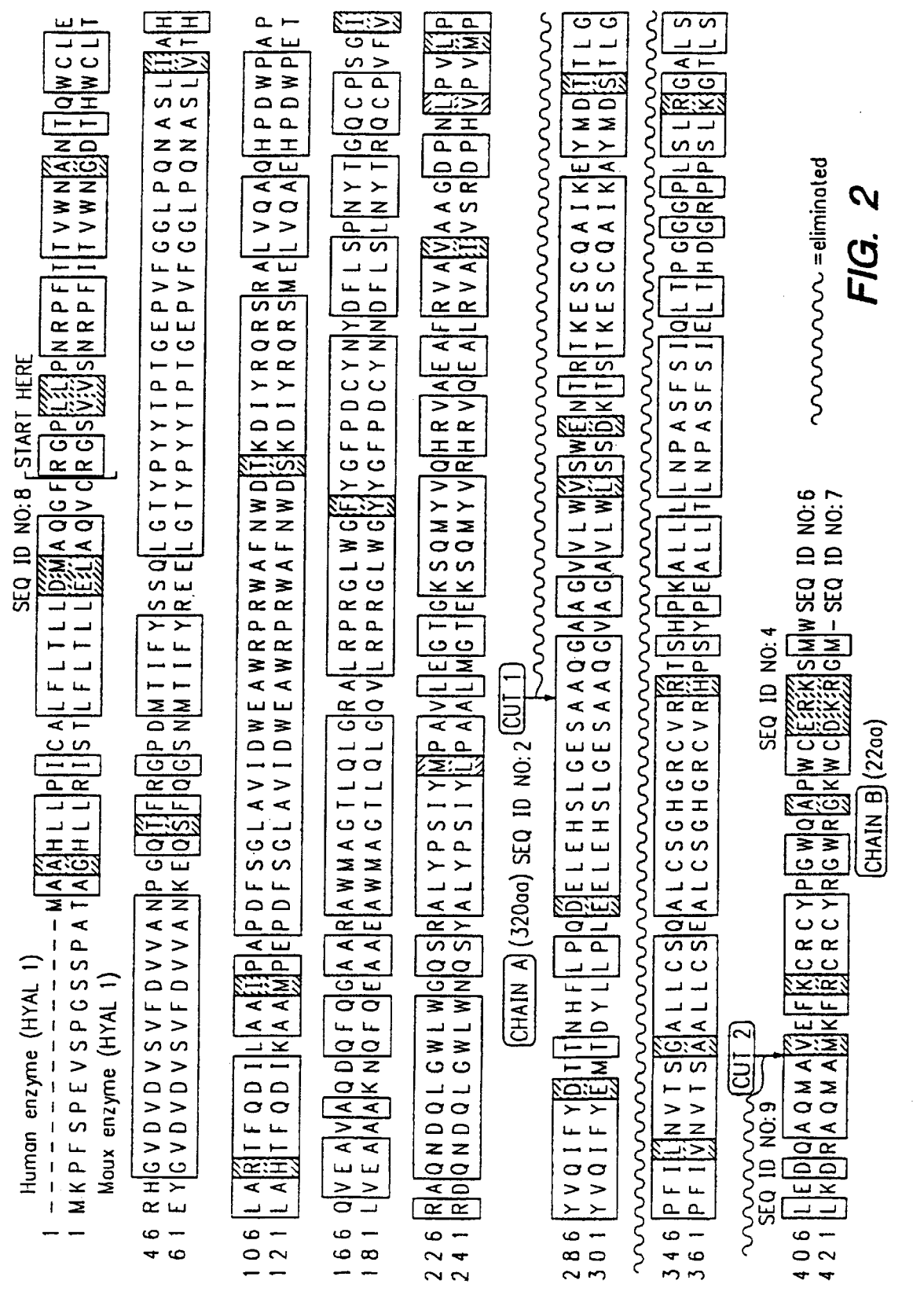
Figure 3:
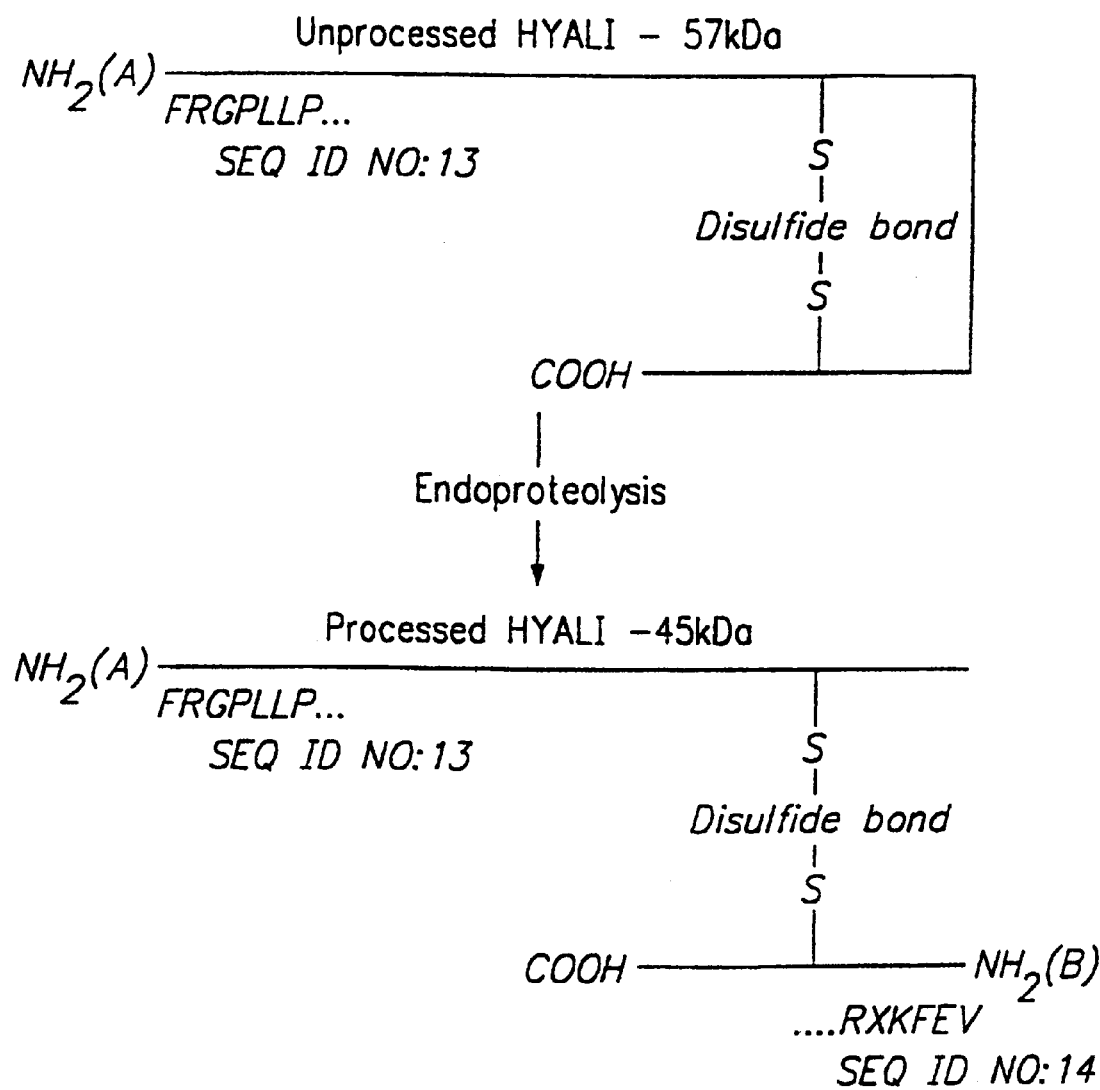
FIG. 3 is a diagrammatic representation of the putative endoproteolytic processing of a plasma HAse to produce a uHAse. Unprocessed plasma HAse is shown in the upper panel. After endoproteolytic processing, two fragments are generated that produces two separate N-termini. The 25 amino acid fragment is presumably linked to the rest of the protein by disulfide bonds. The N-terminal amino acid sequence shown for reference are the common N-terminus of hpHAse and Chain A (SEQ ID NO: 13) and the N-terminus of Chain B (SEQ ID NO: 14).

FIG. 2 is a schematic showing both the homology of huHAse with murine hyal-1, as well as the endoproteolytic cleavage of the hpHAse amino acid sequence to produce the two polypeptides of huHAse, hereinafter referred to as Chain A and Chain B. Chain A is approximately 320 amino acids; Chain B is approximately 20 amino acids. Approximately 93 amino acids are eliminated form the original hpHAse amino acid sequence of 453 amino acids, which includes a signal sequence of approximately 22 amino acids at the N-terminus. FIG. 3 illustrates processing of hpHAse to produce Chain A and Chain B of huHAse, which are then disulfide linked to produce huHAse.

Example 4

Characterization of huHase

Figure 4:
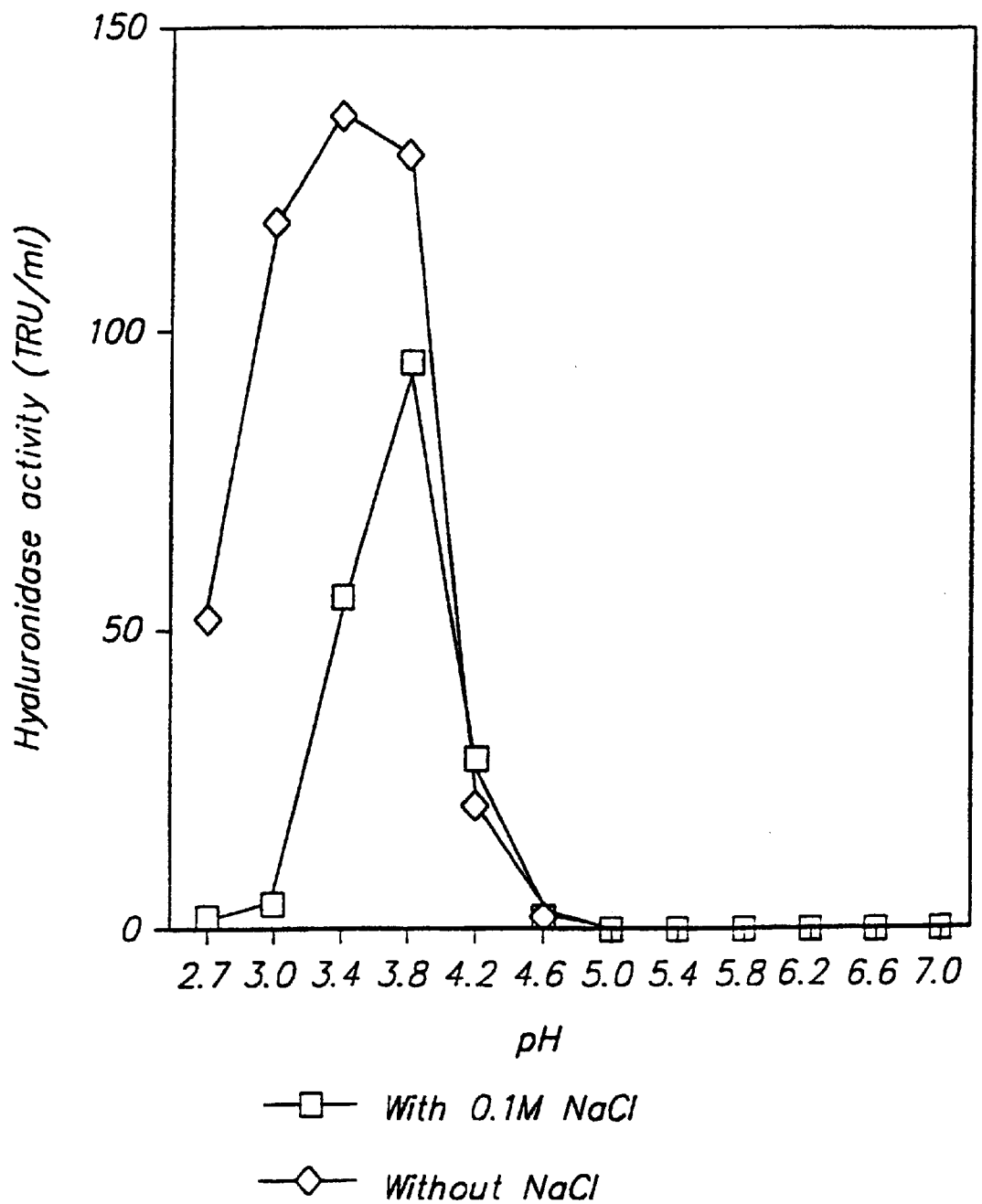
FIG. 4 is a graph showing the pH activity curve of urinary hyaluronidase using the microtiter assay.

Affinity-purified hyaluronidase was diluted 1:500 in 0.1 M citrate-phosphate buffer, and activity was measured by the colorimetric and microtiter assays described above between pH 2.7 and 7.0. Activity was measured in the presence and absence of 0.1 M NaCl. As shown in FIG. 4, huHase had a pH optimum of 3.4 in the absence NaCl. The presence of 0.1 M NaCl caused an increase in the pH optimum to pH 3.8, and a decrease in overall activity. No activity was detected above pH 4.6.

Example 5

Effect of Protease Inhibitors on huHAse

Because of the large volume involved in huHAse purification, protease inhibitors could not be used. Therefore, the effect of proteases on purified urinary HAse activity was tested in order to determine if proteases might have resulted in the production of the lower molecular weight urinary hpHAse isozyme, and thus were only artifacts of the purification process. 50 ml samples of urine were collected directly onto protease inhibitors (Complete protease inhibitor tablets, Boehringer Mannheim, Germany), and concentrated to 2.5 ml on a 8050 Stirred Ultrafiltration Cell (Amicon) fitted with a YM10 membrane. Assays were then performed as described above. Protease inhibitors did not change the characteristics of the urine hyaluronidase, including the appearance of the two isozymes of activity on substrate gel zymography. These data show that the lower molecular weight urinary hpHAse isozyme is not an artifact by non-specific proteases cleavage in the urine, but rather was likely to have been processed prior to voiding, probably in the kidney.

The invention now being fully described, it will be apparent to one of ordinary skill in the art that many changes and modifications can be made thereto without departing from the spirit or scope of the appended claims.

SEQUENCE LISTING

<160> NUMBER OF SEQ ID NOS: 16

<210> SEQ ID NO 1
<211> LENGTH: 933
<212> TYPE: DNA
<213> ORGANISM: H. sapiens

<400> SEQUENCE: 1

| | | | | | |
|---|---|---|---|---|---|
| atggcagccc | acctgcttcc | catctgcgcc | ctcttcctga | ccttactcga | tatggcccaa | 60 |
| ggctttaggg | gccccttgct | acccaaccgg | cccttcacca | ccgtctggaa | tgcaaacacc | 120 |
| cagtggtgcc | tggagaggca | cggtgtggac | gtggatgtca | gtgtcttcga | tgtggtagcc | 180 |
| aacccagggc | agaccttccg | cggccctgac | atgacaattt | tctatagctc | ccagctgggc | 240 |
| acctacccct | actacacgcc | cactggggag | cctgtgtttg | gtggtctgcc | ccagaatgcc | 300 |
| agcctgattg | cccacctggc | ccgcacattc | caggacatcc | tggctgccat | acctgctcct | 360 |
| gacttctcag | gctggcagt | catcgactgg | gaggcatggc | gcccacgctg | ggccttcaac | 420 |
| tgggacacca | aggacattta | ccggcagcgc | tcacgggcac | tggtacaggc | acagcaccct | 480 |
| gattggccag | ctcctcaggt | ggaggcagta | gcccaggacc | agttccaggg | agctgcacgg | 540 |
| gcctggatgg | caggcaccct | ccagctgggg | cgggcactgc | gtcctcgcgg | cctctggggc | 600 |
| ttctatggct | tccctgactg | ctacaactat | gactttctaa | gccccaacta | caccggccag | 660 |
| tgcccatcag | gcatccgtgc | ccaaaatgac | cagctagggt | ggctgtgggg | ccagagccgt | 720 |
| gccctctatc | ccagcatcta | catgcccgca | gtgctggagg | gcacagggaa | gtcacagatg | 780 |
| tatgtgcaac | accgtgtggc | cgaggcattc | cgtgtggctg | tggctgctgg | tgaccccaat | 840 |
| ctgccggtgc | tgccctatgt | ccagatcttc | tatgacacga | caaaccactt | tctgcccctg | 900 |
| gatgagctgg | agcacagcct | gggggagagt | gcg | | | 933 |

<210> SEQ ID NO 2
<211> LENGTH: 311
<212> TYPE: PRT
<213> ORGANISM: H. sapiens

<400> SEQUENCE: 2

Met Ala Ala His Leu Leu Pro Ile Cys Ala Leu Phe Leu Thr Leu Leu
1               5                   10                  15

Asp Met Ala Gln Gly Phe Arg Gly Pro Leu Val Pro Asn Arg Pro Phe
                20                  25                  30

Thr Thr Val Trp Asn Ala Asn Thr Gln Trp Cys Leu Glu Arg His Gly
            35                  40                  45

Val Asp Val Asp Val Ser Val Phe Asp Val Val Ala Asn Pro Gly Gln
        50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
                100                 105                 110

Ile Leu Ala Ala Ile Pro Ala Pro Asp Phe Ser Gly Leu Ala Val Ile
            115                 120                 125

Asp Trp Glu Ala Trp Arg Pro Arg Trp Ala Phe Asn Trp Asp Thr Lys
        130                 135                 140

```
Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Gly Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala
305                 310

<210> SEQ ID NO 3
<211> LENGTH: 71
<212> TYPE: DNA
<213> ORGANISM: H. sapiens

<400> SEQUENCE: 3
ctgtggagtt caaatgtcga tgctaccctg gctggcaggc accgtggtgt gagcggaaga    60
gcatgtggtg a                                                        71

<210> SEQ ID NO 4
<211> LENGTH: 22
<212> TYPE: PRT
<213> ORGANISM: H. sapiens

<400> SEQUENCE: 4

Val Glu Phe Lys Cys Arg Cys Tyr Pro Gly Trp Gln Ala Pro Trp Cys
1               5                   10                  15

Glu Arg Lys Ser Met Trp
            20

<210> SEQ ID NO 5
<211> LENGTH: 1308
<212> TYPE: DNA
<213> ORGANISM: H. sapiens
<220> FEATURE:
<221> NAME/KEY: CDS
<222> LOCATION: (1)...(1305)

<400> SEQUENCE: 5 atg gca gcc cac ctg ctt ccc atc tgc gcc ctc ttc ctg acc tta ctc    48
Met Ala Ala His Leu Leu Pro Ile Cys Ala Leu Phe Leu Thr Leu Leu
1               5                   10                  15 gat atg gcc caa ggc ttt agg ggc ccc ttg cta ccc aac cgg ccc ttc    96
Asp Met Ala Gln Gly Phe Arg Gly Pro Leu Leu Pro Asn Arg Pro Phe
            20                  25                  30 acc acc gtc tgg aat gca aac acc cag tgg tgc ctg gag agg cac ggt   144
```

-continued

```
Thr Thr Val Trp Asn Ala Asn Thr Gln Trp Cys Leu Glu Arg His Gly
         35                  40                  45 gtg gac gtg gat gtc agt gtc ttc gat gtg gta gcc aac cca ggg cag     192
Val Asp Val Asp Val Ser Val Phe Asp Val Val Ala Asn Pro Gly Gln
 50                  55                  60 acc ttc cgc ggc cct gac atg aca att ttc tat agc tcc cag ctg ggc     240
Thr Phe Arg Gly Pro Asp Met Thr Ile Phe Tyr Ser Ser Gln Leu Gly
 65                  70                  75                  80 acc tac ccc tac tac acg ccc act ggg gag cct gtg ttt ggt ggt ctg     288
Thr Tyr Pro Tyr Tyr Thr Pro Thr Gly Glu Pro Val Phe Gly Gly Leu
             85                  90                  95 ccc cag aat gcc agc ctg att gcc cac ctg gcc cgc aca ttc cag gac     336
Pro Gln Asn Ala Ser Leu Ile Ala His Leu Ala Arg Thr Phe Gln Asp
            100                 105                 110 atc ctg gct gcc ata cct gct cct gac ttc tca ggg ctg gca gtc atc     384
Ile Leu Ala Ala Ile Pro Ala Pro Asp Phe Ser Gly Leu Ala Val Ile
            115                 120                 125 gac tgg gag gca tgg cgc cca cgc tgg gcc ttc aac tgg gac acc aag     432
Asp Trp Glu Ala Trp Arg Pro Arg Trp Ala Phe Asn Trp Asp Thr Lys
        130                 135                 140 gac att tac cgg cag cgc tca cgg gca ctg gta cag gca cag cac cct     480
Asp Ile Tyr Arg Gln Arg Ser Arg Ala Leu Val Gln Ala Gln His Pro
145                 150                 155                 160 gat tgg cca gct cct cag gtg gag gca gta gcc cag gac cag ttc cag     528
Asp Trp Pro Ala Pro Gln Val Glu Ala Val Ala Gln Asp Gln Phe Gln
                165                 170                 175 gga gct gca cgg gcc tgg atg gca ggc acc ctc cag ctg ggg cgg gca     576
Gly Ala Ala Arg Ala Trp Met Ala Gly Thr Leu Gln Leu Gly Arg Ala
            180                 185                 190 ctg cgt cct cgc ggc ctc tgg ggc ttc tat ggc ttc cct gac tgc tac     624
Leu Arg Pro Arg Gly Leu Trp Gly Phe Tyr Gly Phe Pro Asp Cys Tyr
            195                 200                 205 aac tat gac ttt cta agc ccc aac tac acc ggc cag tgc cca tca ggc     672
Asn Tyr Asp Phe Leu Ser Pro Asn Tyr Thr Gly Gln Cys Pro Ser Gly
        210                 215                 220 atc cgt gcc caa aat gac cag cta ggg tgg ctg tgg ggc cag agc cgt     720
Ile Arg Ala Gln Asn Asp Gln Leu Gly Trp Leu Trp Gly Gln Ser Arg
225                 230                 235                 240 gcc ctc tat ccc agc atc tac atg ccc gca gtg ctg gag ggc aca ggg     768
Ala Leu Tyr Pro Ser Ile Tyr Met Pro Ala Val Leu Glu Gly Thr Gly
                245                 250                 255 aag tca cag atg tat gtg caa cac cgt gtg gcc gag gca ttc cgt gtg     816
Lys Ser Gln Met Tyr Val Gln His Arg Val Ala Glu Ala Phe Arg Val
            260                 265                 270 gct gtg gct gct ggt gac ccc aat ctg ccg gtg ctg ccc tat gtc cag     864
Ala Val Ala Ala Gly Asp Pro Asn Leu Pro Val Leu Pro Tyr Val Gln
            275                 280                 285 atc ttc tat gac acg aca aac cac ttt ctg ccc ctg gat gag ctg gag     912
Ile Phe Tyr Asp Thr Thr Asn His Phe Leu Pro Leu Asp Glu Leu Glu
        290                 295                 300 cac agc ctg ggg gag agt gcg gcc cag ggg gca gct gga gtg gtg ctc     960
His Ser Leu Gly Glu Ser Ala Ala Gln Gly Ala Ala Gly Val Val Leu
305                 310                 315                 320 tgg gtg agc tgg gaa aat aca aga acc aag gaa tca tgt cag gcc atc    1008
Trp Val Ser Trp Glu Asn Thr Arg Thr Lys Glu Ser Cys Gln Ala Ile
                325                 330                 335 aag gag tat atg gac act aca ctg ggg ccc ttc atc ctg aac gtg acc    1056
Lys Glu Tyr Met Asp Thr Thr Leu Gly Pro Phe Ile Leu Asn Val Thr
            340                 345                 350
```

```
agt ggg gcc ctt ctc tgc agt caa gcc ctg tgc tcc ggc cat ggc cgc      1104
Ser Gly Ala Leu Leu Cys Ser Gln Ala Leu Cys Ser Gly His Gly Arg
        355                 360                 365 tgt gtc cgc cgc acc agc cac ccc aaa gcc ctc ctc ctc ctt aac cct      1152
Cys Val Arg Arg Thr Ser His Pro Lys Ala Leu Leu Leu Leu Asn Pro
370                 375                 380 gcc agt ttc tcc atc cag ctc acg cct ggt ggt ggg ccc ctg agc ctg      1200
Ala Ser Phe Ser Ile Gln Leu Thr Pro Gly Gly Gly Pro Leu Ser Leu
385                 390                 395                 400 cgg ggt gcc ctc tca ctt gaa gat cag gca cag atg gct gtg gag ttc      1248
Arg Gly Ala Leu Ser Leu Glu Asp Gln Ala Gln Met Ala Val Glu Phe
            405                 410                 415 aaa tgt cga tgc tac cct ggc tgg cag gca ccg tgg tgt gag cgg aag      1296
Lys Cys Arg Cys Tyr Pro Gly Trp Gln Ala Pro Trp Cys Glu Arg Lys
        420                 425                 430 agc atg tgg tga                                                      1308
Ser Met Trp
        435

<210> SEQ ID NO 6
<211> LENGTH: 435
<212> TYPE: PRT
<213> ORGANISM: H. sapiens

<400> SEQUENCE: 6

Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255
```

-continued

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
            275                 280                 285

Ile Phe Tyr Asp Thr Thr Asn His Phe Leu Pro Leu Asp Glu Leu Glu
            290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
            325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
            355                 360                 365

Cys Val Arg Arg Thr Ser His Pro Lys Ala Leu Leu Leu Leu Asn Pro
            370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
            405                 410                 415

Lys Cys Arg Cys Tyr Pro Gly Trp Gln Ala Pro Trp Cys Glu Arg Lys
            420                 425                 430

Ser Met Trp
            435

<210> SEQ ID NO 7
<211> LENGTH: 449
<212> TYPE: PRT
<213> ORGANISM: H. sapiens

<400> SEQUENCE: 7

Met Lys Pro Phe Ser Pro Glu Val Ser Pro Gly Ser Ser Pro Ala Thr
1               5                   10                  15

Ala Gly His Leu Leu Arg Ile Ser Thr Leu Phe Leu Thr Leu Leu Glu
            20                  25                  30

Leu Ala Gln Val Cys Arg Gly Ser Val Val Ser Asn Arg Pro Phe Ile
            35                  40                  45

Thr Val Trp Asn Gly Asp Thr His Trp Cys Leu Thr Glu Tyr Gly Val
            50                  55                  60

Asp Val Asp Val Ser Val Phe Asp Val Ala Asn Lys Glu Gln Ser
65                  70                  75                  80

Phe Gln Gly Ser Asn Met Thr Ile Phe Tyr Arg Glu Glu Leu Gly Thr
            85                  90                  95

Tyr Pro Tyr Tyr Thr Pro Thr Gly Glu Pro Val Phe Gly Gly Leu Pro
            100                 105                 110

Gln Asn Ala Ser Leu Val Thr His Leu Ala His Thr Phe Gln Asp Ile
            115                 120                 125

Lys Ala Ala Met Pro Glu Pro Asp Phe Ser Gly Leu Ala Val Ile Asp
            130                 135                 140

Trp Glu Ala Trp Arg Pro Arg Trp Ala Phe Asn Trp Asp Ser Lys Asp
145                 150                 155                 160

Ile Tyr Arg Gln Arg Ser Met Glu Leu Val Gln Ala Glu His Pro Asp
            165                 170                 175

Trp Pro Glu Thr Leu Val Glu Ala Ala Ala Lys Asn Gln Phe Gln Glu

```
                180             185             190
Ala Ala Glu Ala Trp Met Ala Gly Thr Leu Gln Leu Gly Gln Val Leu
            195             200             205

Arg Pro Arg Gly Leu Trp Gly Tyr Tyr Gly Phe Pro Asp Cys Tyr Asn
        210             215             220

Asn Asp Phe Leu Ser Leu Asn Tyr Thr Arg Gln Cys Pro Val Phe Val
225             230             235             240

Arg Asp Gln Asn Asp Gln Leu Gly Trp Leu Trp Asn Gln Ser Tyr Ala
            245             250             255

Leu Tyr Pro Ser Ile Tyr Leu Pro Ala Ala Leu Met Gly Thr Glu Lys
            260             265             270

Ser Gln Met Tyr Val Arg His Arg Val Gln Glu Ala Leu Arg Val Ala
            275             280             285

Ile Val Ser Arg Asp Pro His Val Pro Val Met Pro Tyr Val Gln Ile
        290             295             300

Phe Tyr Glu Met Thr Asp Tyr Leu Leu Pro Leu Glu Leu Glu His
305             310             315             320

Ser Leu Gly Glu Ser Ala Ala Gln Gly Val Ala Gly Ala Val Leu Trp
            325             330             335

Leu Ser Ser Asp Lys Thr Ser Thr Lys Glu Ser Cys Gln Ala Ile Lys
            340             345             350

Ala Tyr Met Asp Ser Thr Leu Gly Pro Phe Ile Val Asn Val Thr Ser
            355             360             365

Ala Ala Leu Leu Cys Ser Glu Ala Leu Cys Ser Gly His Gly Arg Cys
        370             375             380

Val Arg His Pro Ser Tyr Pro Glu Ala Leu Leu Thr Leu Asn Pro Ala
385             390             395             400

Ser Phe Ser Ile Glu Leu Thr His Asp Gly Arg Pro Pro Ser Leu Lys
            405             410             415

Gly Thr Leu Ser Leu Lys Asp Arg Ala Gln Met Ala Met Lys Phe Arg
            420             425             430

Cys Arg Cys Tyr Arg Gly Trp Arg Gly Lys Trp Cys Asp Lys Arg Gly
            435             440             445

Met

<210> SEQ ID NO 8
<211> LENGTH: 21
<212> TYPE: PRT
<213> ORGANISM: H. sapiens

<400> SEQUENCE: 8

Met Ala Ala His Leu Leu Pro Ile Cys Ala Leu Phe Leu Thr Leu Leu
1               5                   10                  15

Asp Met Ala Gln Gly
            20

<210> SEQ ID NO 9
<211> LENGTH: 102
<212> TYPE: PRT
<213> ORGANISM: H. sapiens

<400> SEQUENCE: 9

Ala Gln Gly Ala Ala Gly Val Val Leu Trp Val Ser Trp Glu Asn Thr
1               5                   10                  15

Arg Thr Lys Glu Ser Cys Gln Ala Ile Lys Glu Tyr Met Asp Thr Thr
            20                  25                  30
```

-continued

```
Leu Gly Pro Phe Ile Leu Asn Val Thr Ser Gly Ala Leu Leu Cys Ser
            35                  40                  45
Gln Ala Leu Cys Ser Gly His Gly Arg Cys Val Arg Arg Thr Ser His
 50                  55                  60
Pro Lys Ala Leu Leu Leu Asn Pro Ala Ser Phe Ser Ile Gln Leu
 65                  70                  75                  80
Thr Pro Gly Gly Pro Leu Ser Leu Arg Gly Ala Leu Ser Leu Glu
                 85                  90                  95
Asp Gln Ala Gln Met Ala
             100
```

<210> SEQ ID NO 10
<211> LENGTH: 21
<212> TYPE: PRT
<213> ORGANISM: H. sapiens

<400> SEQUENCE: 10

```
Phe Xaa Gly Pro Leu Leu Pro Asn Arg Pro Phe Thr Thr Val Trp Asn
 1               5                  10                  15
Xaa Asn Thr Gln Trp
             20
```

<210> SEQ ID NO 11
<211> LENGTH: 17
<212> TYPE: PRT
<213> ORGANISM: H. sapiens

<400> SEQUENCE: 11

```
Phe Xaa Gly Pro Leu Leu Pro Asn Xaa Pro Phe Thr Thr Val Trp Asn
 1               5                  10                  15
Ala
```

<210> SEQ ID NO 12
<211> LENGTH: 19
<212> TYPE: PRT
<213> ORGANISM: H. sapiens

<400> SEQUENCE: 12

```
Val Glu Phe Lys Xaa Arg Xaa Tyr Pro Gly Trp Gln Ala Pro Xaa Xaa
 1               5                  10                  15
Glu Arg Lys
```

<210> SEQ ID NO 13
<211> LENGTH: 6
<212> TYPE: PRT
<213> ORGANISM: H. sapiens

<400> SEQUENCE: 13

```
Phe Arg Gly Leu Leu Pro
 1               5
```

<210> SEQ ID NO 14
<211> LENGTH: 6
<212> TYPE: PRT
<213> ORGANISM: H. sapiens

<400> SEQUENCE: 14

```
Val Glu Phe Lys Xaa Arg
 1               5
```

<210> SEQ ID NO 15
<211> LENGTH: 435
<212> TYPE: PRT
<213> ORGANISM: H. sapiens

<400> SEQUENCE: 15

```
Met Ala Gly His Leu Leu Pro Ile Cys Ala Leu Phe Leu Thr Leu Leu
1               5                   10                  15

Asp Met Ala Gln Gly Phe Arg Gly Pro Leu Val Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Gly Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380
```

```
Ala Ser Phe Ser Ile Gln Leu Thr Pro Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
                420                 425                 430

Ser Met Trp
        435

<210> SEQ ID NO 16
<211> LENGTH: 2517
<212> TYPE: DNA
<213> ORGANISM: H. sapiens

<400> SEQUENCE: 16
ttcctccagg agtctctggt gcagctgggg tggaatctgg ccaggccctg cttaggcccc      60
catcctgggg tcaggaaatt tggaggataa ggcccttcag ccccaaggtc agcagggacg     120
agcgggcaga ctggcgggtg tacaggaggg ctgggttgac ctgtccttgg tcactgaggc     180
cattggatct tcctccagtg gctgccagga tttctggtgg aagagacagg aaggcctccc     240
ccccttggtc gggtcagcct gggggctgag ggcctggctg tcagccactc ttcccagaac     300
atatgtcatg gcctcagtgg ctcatgggga agcagggtg ggcgagctta ggctagagca     360
agtcctgtgg gagatggcag aggcctggtc tgagaggcaa ctcggatgtg ccctccagtg     420
gccatgctcc cctccatgcg tctccctgc cctcctggag ccctgcaggt caatgtttaa     480
cagaaaccag agcagcggtg gattaatgcg caagggctca gccccccagc cctgagcagt     540
gggggaatcg gagactttgc aacctgttct cagctctgcc tccctgggc aggttgtcct     600 cgaccagtcc cgtgccatgg caggccacct gcttcccatc tgcgccctct tcctgaccct     660
actcgatatg gccaaggct ttaggggccc cttggtaccc aaccggccct tcaccaccgt     720
ctggaatgca aacacccagt ggtgcctgga gaggcacggt gtggacgtgg atgtcagtgt     780
cttcgatgtg gtagccaacc agggcagac cttccgcggc cctgacatga caattttcta     840
tagctcccag ctgggcacct accctacta cacgcccact ggggagcctg tgtttggtgg     900
tctgccccag aatgccagcc tgattgccca cctggcccgc acattccagg acatcctggc    960
tgccatacct gctcctgact tctcagggct ggcagtcatc gactgggagg catggcgccc   1020
acgctgggcc ttcaactggg acaccaagga catttaccgg cagcgctcac gggcactggt   1080
acaggcacag caccctgatt ggccagctcc tcaggtggag gcagtagccc aggaccagtt   1140
ccagggagct gcacgggcct ggatggcagg caccctccag ctggggggg cactgcgtcc   1200 tcgcggcctc tggggcttct atggcttccc tgactgctac aactatgact ttctaagccc   1260
caactacacc ggccagtgcc catcaggcat ccgtgcccaa aatgaccagc tagggtggct   1320
gtggggccag agccgtgccc tctatcccag catctacatg cccgcagtgc tggagggcac   1380
agggaagtca cagatgtatg tgcaacaccg tgtggccgag gcattccgtg tggctgtggc   1440
tgctggtgac cccaatctgc cggtgctgcc ctatgtccag atcttctatg acacgacaaa   1500
ccactttctg cccctggatg agctggagca cagcctgggg gagagtgcgg cccaggggc   1560 agctggagtg gtgctctggg tgagctggga aaatacaaga accaaggaat catgtcaggc   1620
catcaaggag tatatggaca ctacactggg gcccttcatc ctgaacgtga ccagtggggc   1680
ccttctctgc agtcaagccc tgtgctccgg ccatggccgc tgtgtccgcc gcaccagcca   1740
ccccaaagcc ctcctcctcc ttaaccctgc cagtttctcc atccagctca cgcctggtgg   1800
```

```
tggccccctg agcctgcggg gtgccctctc acttgaagat caggcacaga tggctgtgga    1860
gttcaaatgt cgatgctacc ctggctggca ggcaccgtgg tgtgagcgga agagcatgtg    1920
gtgattggcc acacactgag ttgcacatat tgagaaccta atgcactctg ggtctggcca    1980
gggcttcctc aaatacatgc acagtcatac aagtcatggt cacagtaaag agtacactca    2040
gccactgtca caggcatatt ccctgcacac acatgcatac ttacagactg gaatagtggc    2100
ataaggagtt agaaccacag cagacaccat tcattcctgc tccatatgca tctacttggc    2160
aaggtcatag acaattcctc cagagacact gagccagtct ttgaactgca gcaatcacaa    2220
aggctgacat tcactgagtg cctactcttt gccaatcccc gtgctaagcg ttttatgtgg    2280
acttattcat tcctcacaat gaggctatga ggaaactgag tcactcacat tgagagtaag    2340
cacgttgccc aaggttgcac agcaagaaaa gggagaagtt gagattcaaa cccaggctgt    2400
ctagctccgg gggtacagcc cttgcactcc tactgagttt gtggtaacca gccctgcacg    2460 accectgaat ctgctgagag gcaccagtcc agcaaataaa gcagtcatga tttactt      2517
```

What is claimed is:

1. An isolated human urinary hyaluronidase (huHAse) of about 45 kDa molecular weight comprising a Chain A polypeptide comprising an amino acid sequence of SEQ ID NO: 2, and a Chain B polypeptide comprising an amino acid sequence of SEQ ID NO: 4 wherein said huHAse is substantially free of human plasma hyaluronidase.

2. An isolated Chain A polypeptide of human urinary hyaluronidase (huHAse) comprising an amino acid sequence of SEQ ID NO: 2 wherein said huHAse is substantially free of human plasma hyaluronidase.

3. An isolated Chain B polypeptide of human urinary hyaluronidase (huHAse) comprising an amino acid sequence of SEQ ID NO: 4 wherein said huHAse is substantially free of human plasma hyaluronidase.

4. A formulation for administration of human urinary hyaluronidase (huHAse) to a patient having a condition susceptible to amelioration by administration of huHAse comprising:
   a) a therapeutically effective amount of a human urinary hyaluronidase (huHAse) polypeptide, wherein the huHAse polypeptide comprises a Chain A polypeptide comprising an amino acid sequence of SEQ ID NO: 2 and a Chain B polypeptide comprising an amino acid sequence of SEQ ID NO: 4 wherein said huHAse is substantially free of human plasma hyaluronidase
   b) a pharmaceutically acceptable carrier.

5. An isolated human urinary hyaluronidase (huHAse) comprising a Chain A polypeptide comprising an amino acid sequence of SEQ ID NO: 2, and a Chain B polypeptide comprising an amino acid sequence of SEQ ID NO: 4, wherein the Chain A polypeptide and the Chain B polypeptide are joined by a disulfide bond wherein, said huHAse is substantially free of human plasma hyaluronidase.

6. An isolated human urinary hyaluronidase (huHAse) of about 45 kDa comprising a Chain A polypeptide encoded by a polynucleotide sequence of SEQ NO: 1, and a Chain B polypeptide encoded by a polynucleotide of SEQ ID NO: 3, wherein said huHAse is substantially free of human plasma hyaluronidase.

7. An isolated Chain A polypeptide of human urinary hyaluronidase (huHAse) comprising an amino acid sequence encoded by a polynucleotide of SEQ ID NO: 1, wherein said huHAse is substantially free of human plasma hyaluronidase.

8. An isolated Chain B polypeptide of human urinary hyaluronidase (huHAse) comprising an amino acid sequence encoded by a polynucleotide of SEQ ID NO: 3 wherein said huHAse is substantially free of human plasma hyaluronidase.

9. A human urinary hyaluronidase (huHAse) of about 45 kDa molecular weight comprising a Chain A polypeptide comprising an amino acid sequence of SEQ ID NO: 2, and a Chain B polypeptide comprising an amino acid sequence of SEQ ID NO: 4, wherein said huHAse is substantially free of human plasma hyaluronidase.

* * * * *